(12) United States Patent
Agarwal et al.

(10) Patent No.: US 11,642,379 B2
(45) Date of Patent: May 9, 2023

(54) HEMATOPOIETIC STEM CELL ENGRAFTMENT

(71) Applicants: The Board of Trustees of the Leland Stanford Junior University, Stanford, CA (US); The Regents of the University of California, Oakland, CA (US)

(72) Inventors: Rajni Agarwal, Redwood City, CA (US); Janel Long Boyle, Redwood City, CA (US); Morton J. Cowan, Kentfield, CA (US); Christopher Dvorak, Redwood City, CA (US); Hye Sook Kwon, Redwood City, CA (US); Anne Le, Redwood City, CA (US); Aaron Logan, Redwood City, CA (US); Wendy Pang, Redwood City, CA (US); Robertson Parkman, Redwood City, CA (US); Maria-Grazia Roncarolo, Menlo Park, CA (US); Kenneth Weinberg, Stanford, CA (US); Judith A. Shizuru, Palo Alto, CA (US); Susan Sweeney Prohaska, Mountain View, CA (US); Agnieszka Czechowicz, Stanford, CA (US); Irving L. Weissman, Stanford, CA (US)

(73) Assignees: The Board of Trustees of the Leland Stanford Junior University, Stanford, CA (US); The Regents of the University of California, Oakland, CA (US)

(*) Notice: Subject to any disclaimer, the term of this patent is extended or adjusted under 35 U.S.C. 154(b) by 147 days.

(21) Appl. No.: 16/768,016

(22) PCT Filed: Dec. 7, 2018

(86) PCT No.: PCT/US2018/064462
§ 371 (c)(1),
(2) Date: May 28, 2020

(87) PCT Pub. No.: WO2019/113437
PCT Pub. Date: Jun. 13, 2019

(65) Prior Publication Data
US 2021/0369782 A1   Dec. 2, 2021

Related U.S. Application Data

(60) Provisional application No. 62/596,307, filed on Dec. 8, 2017.

(51) Int. Cl.
| | |
|---|---|
| A61K 39/395 | (2006.01) |
| A61K 35/28 | (2015.01) |
| A61P 37/06 | (2006.01) |
| A61K 39/00 | (2006.01) |
| A61N 5/10 | (2006.01) |

(52) U.S. Cl.
CPC .......... *A61K 35/28* (2013.01); *A61K 39/3955* (2013.01); *A61P 37/06* (2018.01); *A61K 2039/505* (2013.01); *A61K 2039/545* (2013.01); *A61N 5/10* (2013.01)

(58) Field of Classification Search
None
See application file for complete search history.

(56) References Cited

U.S. PATENT DOCUMENTS

| 10,072,091 B2 | 9/2018 | Weissman et al. |
| 2016/0004667 A1 | 1/2016 | Chakerian et al. |
| 2016/0032498 A1 | 1/2016 | Kübler et al. |
| 2017/0022473 A1 | 1/2017 | Murakami et al. |

OTHER PUBLICATIONS

Baum et al. (1992) "Isolation of a candidate human hematopoietic stem-cell population" PNAS 89 (7) 2804-2808.
Czechowicz et al. (2007) "Efficient Transplantation via Antibody-based Clearance of Hematopoietic Stem Cell Niches" Science. 318(5854): 1296-1299.
Majeti et al. (2007) "Identification of a hierarchy of multipotent hematopoietic progenitors in human cord blood" Cell Stem Cell 1(6):635-45.
Muller et al. (2012) "Long-term outcome of patients with metastatic breast cancer treated with high-dose chemotherapy and transplantation of purified autologous hematopoietic stem cells". Biol Blood Marrow Transplant. 18(1): 125-33.
Negrin et al (2000) "Transplantation of highly purified CD34+Thy-1+ hematopoietic stem cells in patients with metastatic breast cancer" Biol Blood Marrow Transplant 6(3):262-71.
Uchida et al. (1998) "High doses of purified stem cells cause early hematopoietic recovery in syngeneic and allogeneic hosts". J Clin Invest. 101(5): 961-6.

*Primary Examiner* — Joanne Hama
*Assistant Examiner* — Fozia M Hamud
(74) *Attorney, Agent, or Firm* — Pamela J. Sherwood; Bozicevic, Field & Francis LLP

(57) ABSTRACT

The present invention provides clinical evidence for a method of stem cell transplantation that facilitates engraftment and reconstitutes immunocompetence of the recipient without requiring myeloablative conditioning.

17 Claims, 14 Drawing Sheets

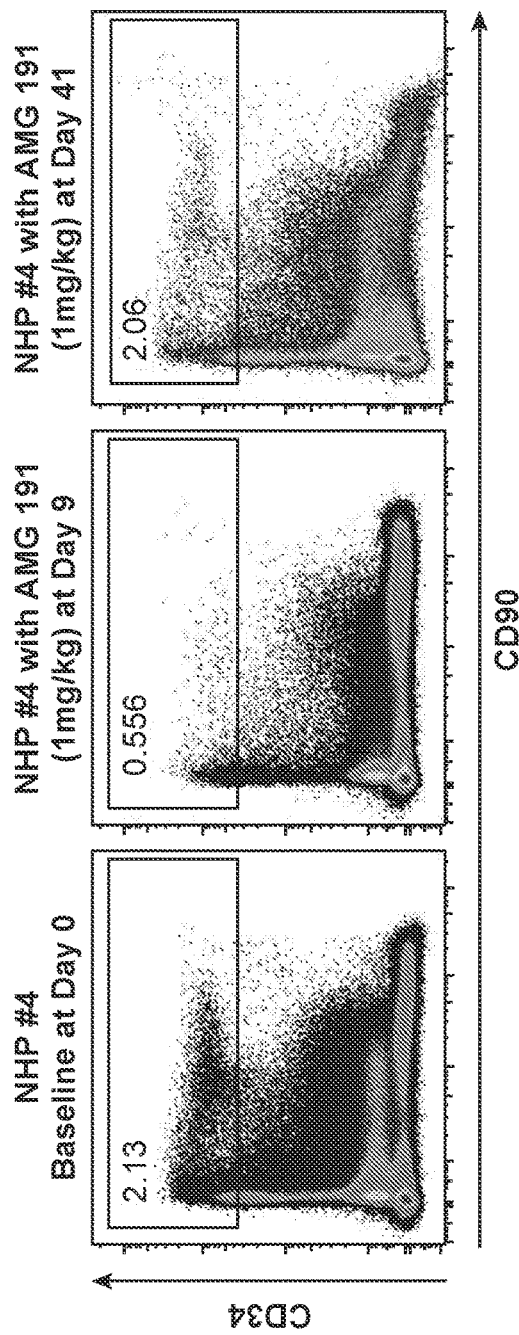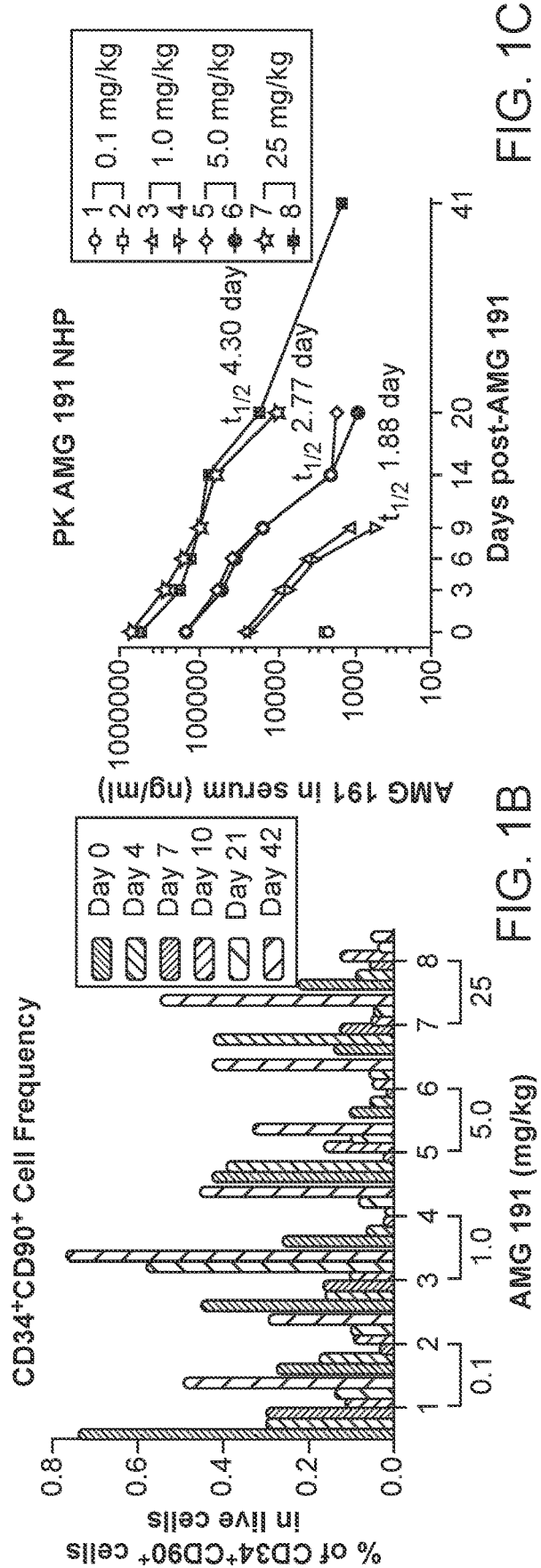

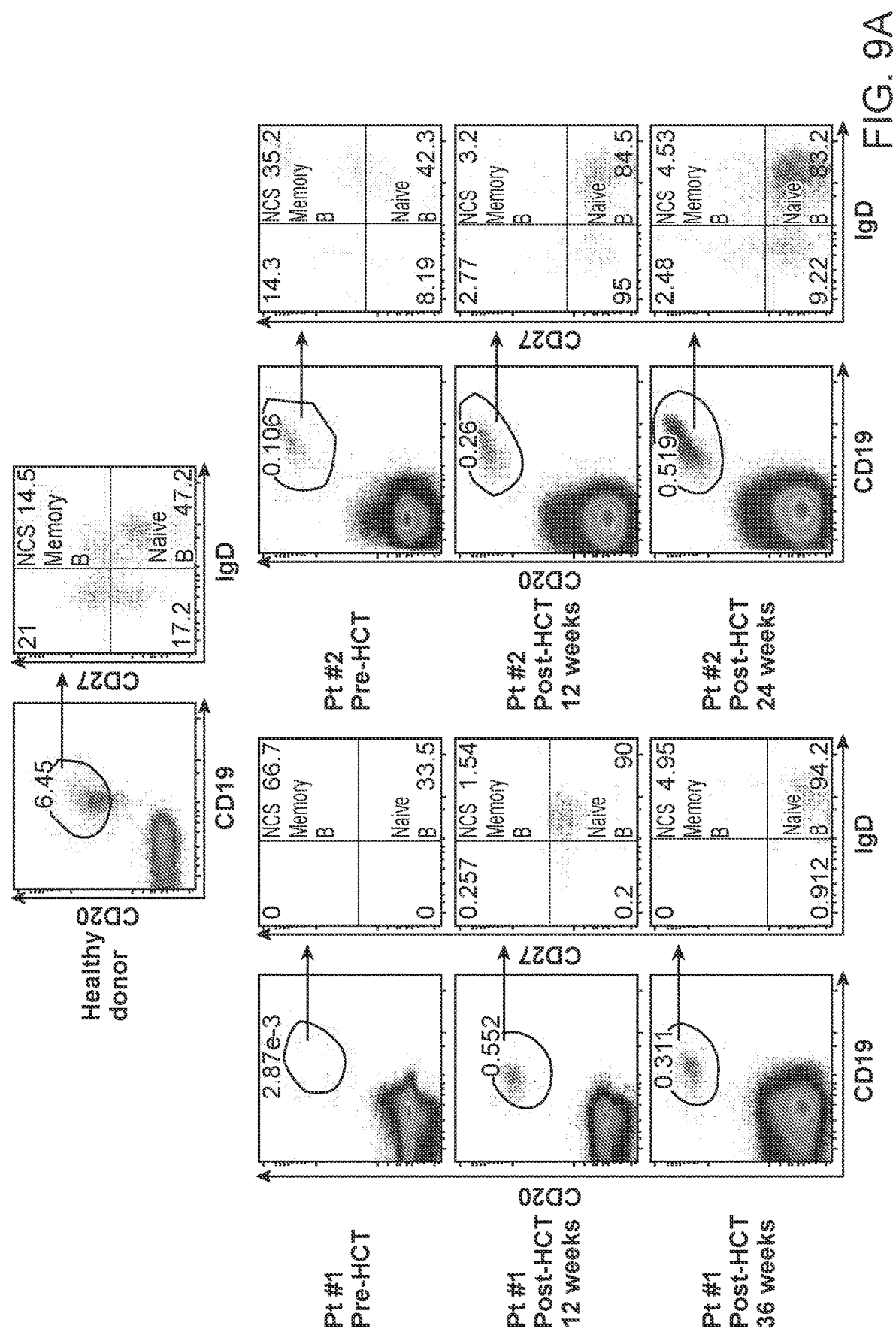

HEMATOPOIETIC STEM CELL ENGRAFTMENT

CROSS-REFERENCE

This application claims the benefit of U.S. Provisional Patent Application No. 62/596,307 filed Dec. 8, 2017, which application is incorporated herein by reference in its entirety.

Stem cells provide the means for organisms to maintain and repair certain tissues, through the ability of these cells to self-renew and to generate differentiated cells. Clinically, bone marrow and hematopoietic stem cell transplantation are widely used as a means of providing patients with the capacity to generate blood cells, usually where the patient has been depleted of endogenous stem cells by high dose chemotherapy or radiation.

Hematopoietic cell transplantation (HCT) generally involves the intravenous infusion of autologous or allogeneic blood forming cells, the active subset of which are hematopoietic stem cells [HSC]; these are collected from bone marrow, peripheral blood, or umbilical cord blood and transplanted to reestablish hematopoietic function in patients whose bone marrow or immune system is damaged or defective. This procedure is often performed as part of therapy to eliminate a bone marrow infiltrative process, such as leukemia, or to correct congenital immunodeficiency disorders. In addition, HCT is used to allow patients with cancer to receive higher doses of chemotherapy than bone marrow can usually tolerate; bone marrow function is then salvaged by replacing the marrow with previously harvested stem cells. HCT can also be performed to induce immune tolerance to donor matched solid organ grafts or block autoimmune pathogenesis in patients with autoimmune disorders. Enriched or purified populations of HSC can also be transplanted, and are not contaminated with other cells, many of which are deleterious to the host.

The list of diseases for which HSCT is being used is rapidly increasing. More than half of the autologous transplantations are performed for multiple myeloma and non-Hodgkin lymphoma and a vast majority of allogeneic transplants are performed for hematologic and lymphoid cancers.

The preparative or conditioning regimen is a critical element in hematopoietic cell transplantation (HCT). In a successful transplantation, clearance of bone-marrow niches must be achieved for donor hematopoietic stem cell (HSC) to engraft. The preparative regimen may also provide immunosuppression sufficient to prevent rejection of transplanted genetically disparate grafts, and to eradicate the disease for which the transplantation is being performed. Current methods to clear niche space rely on radiation and/or chemotherapy, which can impart toxic adverse effects that greatly limit the potential clinical utility of BMT. Traditionally, myeloablative conditioning is performed.

Myeloablative regimens can be classified as radiation-containing or non-radiation-containing regimens: therapies that were developed by escalating the dose of radiation or of a particular drug to the maximally tolerated dose. Total-body irradiation and cyclophosphamide or busulfan and cyclophosphamide are the commonly used myeloablative therapies. These regimens are especially used in aggressive malignancies, such as leukemias. However, such treatment carries a number of disadvantages in terms of toxicity to the patient. Reduced intensity conditioning (RIC) or non-myeloablative regimens are also used to obtain engraftment of HSC allowing HCT to be used for a broader array of patients. However, these regimens, while less intense still rely on radiation and/or chemotherapy to achieve engraftment and toxicities from these regimens are still problematic and the effect of eliminating the underlying diseased blood stem cells is weaker than myeloablative regimens.

Improved methods for engraftment of stem cells, including hematopoietic stem cells, are of great clinical interest. The present invention addresses this need.

SUMMARY OF THE INVENTION

Methods are provided for engraftment of hematopoietic stem cells, in a recipient with a pre-transplantation conditioning regimen comprising administration of an antibody specific for CD117 in a dose sufficient to empty hematopoietic stem cell (HSC) niches to permit HSC engraftment in the recipient, followed by transplantation of donor allogeneic or gene-modified HSC. The transplantation is performed in the absence of myeloablative conditioning. In some embodiments the recipient is immunocompetent. In some embodiments that recipient is partially or highly immune deficient. In some embodiments the depletion antibody is a humanized monoclonal antibody, which may be an aglycosylated IgG antibody. In some embodiments the antibody is the IgG1 antibody AMG-191, described in U.S. Pat. No. 8,436,150, herein specifically incorporated by reference. In certain embodiments the antibody is the sole depletion agent.

In some embodiments an individual with severe combined immunodeficiency (SCID) is treated by administration of an antibody specific for CD117 in a dose sufficient to empty hematopoietic stem cell (HSC) niches to permit HSC engraftment in the recipient, followed by transplantation of donor HSC, in the absence of myeloablative conditioning.

In some embodiments, an individual with myelodysplastic disease, e.g. myelodysplastic syndrome (MDS), or acute myelogenous leukemia (AML), particularly AML secondary to MDS, is treated with a non-myeloablative conditioning regimen of total lymphoid irradiation (TLI) and anti-thymocyte globulin (ATG), combined with administration of an antibody specific for CD117 in a dose sufficient to empty hematopoietic stem cell (HSC) niches to facilitate HSC engraftment in the recipient. Following such ablation of HSC niches, the individual is transplanted with HSC. In some embodiments the individual is fully chimeric for the donor HSC following engraftment. In some embodiments the individual is partially chimeric for donor HSC following engraftment.

In some embodiments, a single dose of the depletion antibody is administered prior to transplantation. In some embodiments the dose of antibody is delivered by intravenous infusion over a short period of time, e.g. over less than about 4 hours, less than about 2 hours, or for around about 1 hour. The dose of antibody may be up to about 1.2 mg/kg, up to about 0.95 mg/kg; up to about 0.6 mg/kg; up to about 0.3 mg/kg; up to about 0.1 mg/kg. Surprisingly it has been found that a low dose of antibody, for example up to about 0.1 mg/kg, is sufficient to achieve a clinically relevant result.

Methods described herein find use in the treatment of a variety of blood disorders, e.g. genetic disorders including aplastic anemia; Fanconi anemia; sickle cell disease; thalassemias; severe immunodeficiency; bone marrow failure states, immune deficiencies, hemoglobinopathies, leukemias, lymphomas, immune-tolerance induction, genetic disorders treatable by bone marrow transplantation and other blood disorders, myelodysplastic syndrome, and the like. In some embodiments the recipient has severe combined immunodeficiency (SCID). In some embodiments the recipient has myelodysplastic syndrome. Methods described herein also find use in the treatment of a variety of autoimmune disorders e.g., Lupus, 1D, scleroderma, MS and the like and as means of inducing tolerance to solid organ transplants (e.g., kidney, liver, heart, lung), and for the treatment of human immunodeficiency virus (HIV) infection.

BRIEF DESCRIPTION OF THE DRAWINGS

FIGS. 1A-1C. Non-human Primate HSC—Depleted by AMG 191. (A) Representative FACS plot showing CD34$^+$ cells in BM of NHP #4 animal on days 0 (before AMG 191 treatment), 10, and 42 post administration of 1.0 mg/kg AMG 191. CD34$^+$ cells were gated from live cells. (B) Frequency of CD34$^+$ cells amongst live cells in BM aspirates obtained from each NHP. BM aspirates were collected from individual NHPs (2 animals for each dose group) prior to the administration of AMG 191 (baseline, designated as day 0), and on days 4, 7, 10, 21, 42 post-administration. AMG 191 was infused into animals on day 1. (C) AMG 191 is cleared in the serum of NHP in a dose dependent manner. The highest levels of AMG 191 in serum of all animals were observed at the first-time point collection (5 min after dose administration on Day 1). Antibody levels measured on day 4 in the 0.1 mg/kg group fell below the assay detection limit of 50 ng/ml. The level of AMG 191 in serum was analyzed and terminal elimination half-life ($t_{1/2}$) was determined. The averages of half-life ($t_{1/2}$) obtained from two animals of each group are presented. Colors correspond to days relative to infusion. Animal identification (1 through 8) and dose level is shown on the X-axis.

(FIG. 3A) AMG 191 inhibits proliferation of human BM HSCs in a dose-dependent manner. BM human HSCs were plated in media supplemented with hSCF, hTPO, and hFlt-3L and treated with AMG 191 at 0.01-10 μg/ml or left untreated. (FIG. 3B) AMG 191 inhibits hematopoiesis of human BM-derived CD34$^+$CD90$^+$ cells in vitro. AMG 191 markedly reduced methylcellulose colonies of BFU-E and CFU-GEMM. Lesser inhibitory effects of AMG 191 were noted on the more differentiated CFU-GM/G/M.

(FIG. 4A) AMG 191 depletes human HSPCs engrafted in NSG mice. Frequency of human HSPC amongst all live cells present in BM aspirates obtained from humanized NSG mice treated with 0.3 mg/kg (left panel) and 1.0 mg/kg AMG 191 (right panel). P-values were obtained using paired student t-test. (FIG. 4B) Second human donor engraftment level correlates with AMG 191 dose. Six weeks after HCT, chimerism was accessed in BM of transplanted humanized NSG mice. Secondary engraftment was measured by the frequency of mCitrine expressing cells in each cell subset. Cell frequency was analyzed by FACS and FlowJo software. P-values were obtained using unpaired student t-test and Prism software. Data and error bars represent the mean±sem.

(FIG. 6A): AMG 191 is cleared in NHP serum in a dose dependent manner. Serum AMG 191 was analyzed and terminal elimination half-life (t½) determined. Averages of t½ obtained from 2 NHP/group are shown. (FIG. 6B) Representative FACS showing CD34+ cells in BM of NHP #4 on days 0 (before AMG 191), 10, and 42 post-AMG 191 of 1.0 mg/kg AMG 191. (FIG. 6C) Frequency of CD34+ cells amongst live cells in BM aspirates from each NHP. BM aspirates were collected from NHPs (2/group) prior to AMG 191 (baseline—day 0), and days 4, 7, 10, 21, 42 post-AMG 191. Colors correspond to days relative to infusion. (FIG. 6D) Effect of AMG 191 on red cell parameters. Hemoglobin and reticulocyte count from individual NHP before AMG 191 (day 0) and post-infusion. Colored lines correspond to individual NHP, doses shown on right.

FIGS. 9A-9B: T and B cell reconstitution in Pts 1 and 2 at time points after AMG 191 conditioned HCT. (FIG. 9A) FACS of blood B cells in Pts #1 and #2 pre- and post-HCT. Prior to HCT Pt #1 had no blood CD19$^+$CD20$^+$ B cells and Pt #2 had low but detectable levels. Post-HCT both show increased and sustained levels. Extended phenotype analysis show naïve B comprise most of the CD19$^+$CD20$^+$ cells. (FIG. 9B) Absolute counts of T cell subtypes in the blood of Pt #1 pre- and post-AMG 191 conditioned HCT.

chimerism on pre-treatment Day 0 and at Day 21 and 12 weeks after completion of treatment with AMG 191. Purified low risk MDS HSCs were transplanted into sub-lethally irradiated immune deficient mice and baseline myeloid chimerism was obtained on "Day 0," which was ~12 weeks after initial establishment of xenografts. Xenografted mice were treated with 75 μg of AMG 191 administered intravenously (IV) on Day 1. Colored lines are results from individual animals.

Figure 12:
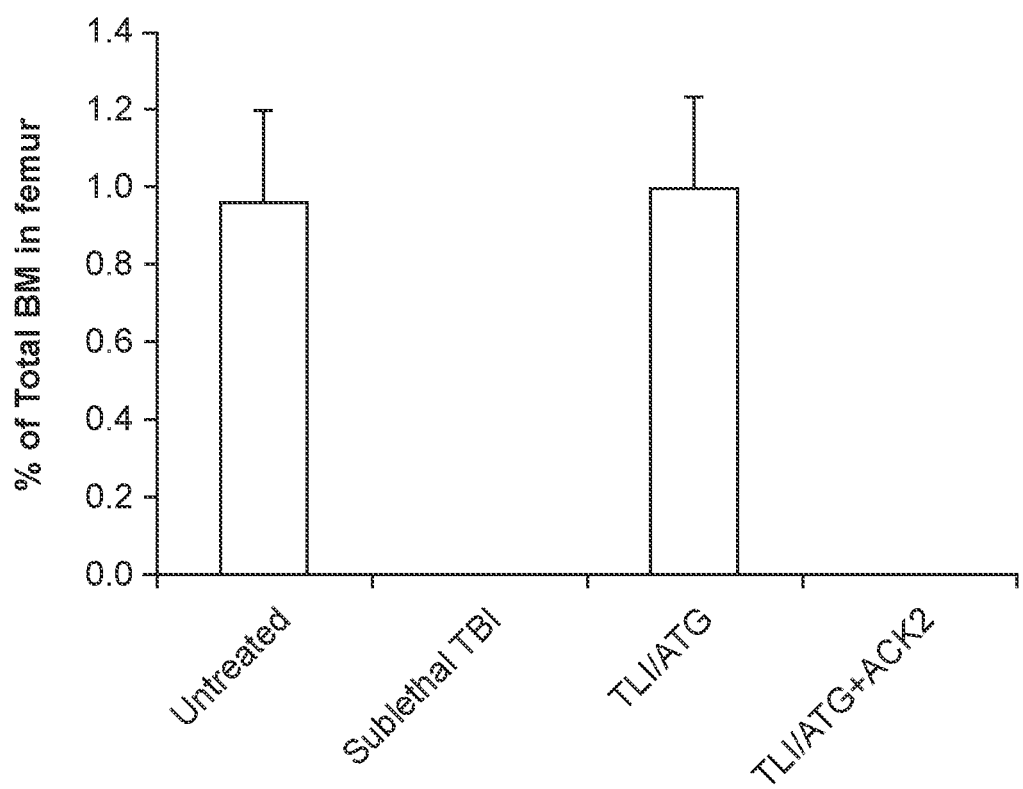

FIG. 12: Depletion of HSCs following TBI, TLI/ATG, and ACK2+TLI/ATG. Anti-mouse CD117 antibody, ACK2, depletes HSC in the femurs of mice conditioned with TLI/ATG. Shown are the percent of HSC of the total bone marrow cells present in the femurs of mice at the end of conditioning with TLI/ATG plus ACK2 compared to mice treated with TLI/ATG only and controls that were either untreated or that received sublethal total body irradiation. Substantial HSC depletion of the shielded femurs is observed.

DETAILED DESCRIPTION OF THE EMBODIMENTS

Methods are provided for the engraftment of stem cells in a subject, where endogenous stem cells are selectively depleted with an anti-CD117 antibody. Following depletion, and after a period of time sufficient to substantially eliminate the depleting antibodies from the patient circulation, exogenous HSC are introduced to the patient.

To facilitate an understanding of the invention, a number of terms are defined below.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Definitions

P41 Stem cell markers. In one embodiment of the invention, the marker for depletion is c-kit (CD117). CD117 is a receptor tyrosine kinase type Ill, which binds to stem cell factor (a substance that causes certain types of cells to grow), also known as "steel factor" or "c-kit ligand". When this receptor binds to stem cell factor (SCF) it forms a dimer that activates its intrinsic tyrosine kinase activity, that in turn phosphorylates and activates signal transduction molecules that propagate the signal in the cell. See, for example, the human refseq entries Genbank NM_000222; NP_000213. CD117 is an important cell surface marker used to identify certain types of hematopoietic (blood) progenitors in the bone marrow. Hematopoietic stem cells (HSC), multipotent progenitors (MPP), and common myeloid progenitors (CMP) express high levels of CD117. A number of antibodies that specifically bind human CD117 are known in the art and commercially available, including without limitation SR1, 2B8, ACK2, YB5-B8, 57A5, 104D2, etc. Of particular interest is the humanized form of SR1, AMG 191, described in U.S. Pat. Nos. 8,436,150, and 7,915,391 which is an aglycosylated IgG1 humanized antibody.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies.

Selection of antibodies for depletion may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies. The cross-linking of Fc receptors signals the effector cells to kill the target cells by cytolysis or apoptosis. In one embodiment, the induction is achieved via antibody-dependent cellular cytotoxicity (ADCC).

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus pepsin digests an antibody below the disulfide linkages in the hinge region to produce F(ab)'$_2$, a dimer of Fab which itself is a light chain joined to $V_H$-$C_{H1}$ by a disulfide bond. The F(ab)'2 may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin. The humanized antibody may be conjugated to a toxin to form an antibody drug conjugate (ADC).

Antibodies of interest for ablation may be tested for their ability to induce ADCC (antibody-dependent cellular cytotoxicity). Antibody-associated ADCC activity can be monitored and quantified through detection of either the release of label or lactate dehydrogenase from the lysed cells, or detection of reduced target cell viability (e.g. annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.). Preferably, the antibodies of the present invention induce at least 10%, 20%, 30%, 40%, 50%, 60%, or 80% cytotoxicity of the target cells. In some embodiments, the antibody is free of cytotoxic adjuncts or conjugates.

The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages.

For engraftment purposes, a composition comprising hematopoietic stem cells, is administered to a patient. Such methods are well known in the art. The stem cells are optionally, although not necessarily, purified. Abundant reports explore various methods for purification of stem cells and subsequent engraftment, including flow cytometry; an isolex system (Klein et al. (2001) Bone Marrow Transplant. 28(11):1023-9; Prince et al. (2002) Cytotherapy 4(2): 137-45); immunomagnetic separation (Prince et al. (2002) Cytotherapy 4(2):147-55; Handgretinger et al. (2002) Bone Marrow Transplant. 29(9):731-6; Chou et al. (2005) Breast Cancer. 12(3):178-88); and the like. Each of these references is herein specifically incorporated by reference, particularly with respect to procedures, cell compositions and doses for hematopoietic stem cell transplantation.

Hematopoietic stem cells can be obtained by harvesting from bone marrow or from peripheral blood. Bone marrow is generally aspirated from the posterior iliac crests while the donor is under either regional or general anesthesia. Additional bone marrow can be obtained from the anterior iliac crest. A dose of $1\times10^8$ and $2\times10^8$ marrow mononuclear cells per kilogram is generally considered desirable to establish engraftment in autologous and allogeneic marrow transplants, respectively. Bone marrow can be primed with granulocyte colony-stimulating factor (G-CSF; filgrastim [Neupogen]) to increase the stem cell count.

Mobilization of stem cells from the bone marrow into peripheral blood by cytokines such as G-CSF or GM-CSF has led to the widespread adoption of peripheral blood progenitor cell collection by apheresis for hematopoietic stem cell transplantation. The dose of G-CSF used for mobilization is 10 µg/kg/day. In autologous donors who are heavily pretreated, however, doses of up to 40 µg/kg/day can be given. Mozobil may be used In conjunction with G-CSF to mobilize hematopoietic stem cells to peripheral blood for collection.

The cells which are employed may be fresh, frozen, or have been subject to prior culture. They may be fetal, neonate, adult, etc. Hematopoietic stem cells may be obtained from fetal liver, bone marrow, blood, particularly G-CSF or GM-CSF mobilized peripheral blood, or any other conventional source. Cells for engraftment are optionally isolated from other cells, where the manner in which the stem cells are separated from other cells of the hematopoietic or other lineage is not critical to this invention. If desired, a substantially homogeneous population of stem or progenitor cells may be obtained by selective isolation of cells free of markers associated with differentiated cells, while displaying epitopic characteristics associated with the stem cells.

Cells may be genetically altered in order to introduce genes useful in the differentiated cell, e.g. repair of a genetic defect in an individual, selectable marker, etc., or genes useful in selection against undifferentiated ES cells. Cells may also be genetically modified to enhance survival, control proliferation, and the like. Cells may be genetically altering by transfection or transduction with a suitable vector, homologous recombination, or other appropriate technique, so that they express a gene of interest. In one embodiment, cells are transfected with genes encoding a telomerase catalytic component (TERT), typically under a heterologous promoter that increases telomerase expression beyond what occurs under the endogenous promoter, (see International Patent Application WO 98/14592). In other embodiments, a selectable marker is introduced, to provide for greater purity of the desired differentiating cell. Cells may be genetically altered using vector containing supernatants over an 8-16 h period, and then exchanged into growth medium for 1-2 days. Genetically altered cells are selected using a drug selection agent such as puromycin, G418, or blasticidin, and then recultured.

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is constitutive, pan-specific, specifically active in a differentiated cell type, etc. Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

Gene editing technologies such as CRISPR/CAS9 systems can be used for altering genes in the transplanted cells. Alternatively many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells. Combinations of retroviruses and an appropriate packaging line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line. The vectors may include genes that must later be removed, e.g. using a recombinase system such as Cre/Lox, or the cells that express them destroyed, e.g. by including genes that allow selective toxicity such as herpesvirus TK, bcl-xs, etc.

A "patient" for the purposes of the present invention includes humans, other mammals and mammals used in laboratories for human care. Thus the methods provide clinical results from human patients.

Additional terms. The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted as well as those in which prevention is desired.

Myelodysplastic syndrome (MDS). The myelodysplastic syndromes (MDS) are classified according to features of cellular morphology, etiology, clinical presentation, and cytogenetic and molecular features. The morphological classification of the MDS is largely based on the percent of myeloblasts in the bone marrow and blood, the type and degree of myeloid dysplasia, and the presence of ringed sideroblasts. The clinical classification of the MDS depends upon whether there is an identifiable etiology, the nature of the molecular or chromosomal abnormalities and whether the MDS has been treated previously. Current classification of MDS cellular types and subtypes are listed below.

Included in MDS is Refractory anemia (RA). In patients with RA, the myeloid and megakaryocytic series in the bone marrow appear normal to conventional tests, but megaloblastoid erythroid hyperplasia is present. Dysplasia is usually minimal. Marrow blasts are less than 5%, and no peripheral blasts are present. Macrocytic anemia with reticulocytopenia is present in the blood. Transformation to acute leukemia is rare, and median survival varies from 2 years to 5 years in most series.

Refractory anemia with ringed sideroblasts (RARS). In patients with RARS, the blood and marrow are identical to those in patients with RA, except that at least 15% of marrow red cell precursors are ringed sideroblasts. Prognosis is similar to that of RA.

Refractory anemia with excess blasts (RAEB). In patients with RAEB, there is significant evidence of disordered myelopoiesis and megakaryocytopoiesis in addition to abnormal erythropoiesis. Because of differences in prognosis related to progression to a frank AML, this cellular classification is comprised of two categories, refractory anemia with excess blasts-1 (RAEB-1) and refractory anemia with excess blasts-2 (RAEB-2). Combined, the two categories account for approximately 40% of all patients with MDS. RAEB-1 is characterized by 5% to 9% blasts in the bone marrow and less than 5% blasts in the blood. Approximately 25% of cases of RAEB-1 progress to AML. Median survival is approximately 18 months. RAEB-2 is characterized by 10% to 19% blasts in the bone marrow. Approximately 33% of cases of RAEB-2 progress to AML. Median survival for RAEB-2 is approximately 10 months.

Refractory cytopenia with multilineage dysplasia (RCMD). In patients with RCMD, bicytopenia or pancytopenia is present. In addition, dysplastic changes are present in 10% or more of the cells in two or more myeloid cell lines. There are less than 1% blasts in the blood and less than 5% blasts in the bone marrow. Auer rods are not present. Monocytes in the blood are less than $1 \times 10^9$. RCMD accounts for approximately 24% of cases of MDS. The frequency of evolution to acute leukemia is 11%. The overall median survival is 33 months. Refractory cytopenia with multilineage dysplasia and ringed sideroblasts (RCMD-RS) represents another category of RMDS. In RCMD-RS, features of RCMD are present, and more than 15% of erythroid precursors in the bone marrow are ringed sideroblasts. RCMD-RS accounts for approximately 15% of cases of MDS. Survival in RCMD-RS is similar to that in primary RCMD.

Myelodysplastic syndrome associated with an isolated del(5q) chromosome abnormality is associated with an isolated del(5q) cytogenetic abnormality. Blasts in both blood and bone marrow are less than 5%. This subtype is associated with a long survival.

The mainstay of treatment of the myelodysplastic syndromes (MDS) has conventionally been supportive care. The use of erythropoietin may improve anemia, although effective treatment may require substantially higher doses of erythropoietin than are used for other indications (150-300 µg/kg/day).

Acute myelogenous leukemia (AML). Acute myelogenous leukemia involves malignant transformation and uncontrolled proliferation of an abnormally differentiated, long-lived progenitor cell that results in high circulating numbers of immature blood forms and replacement of normal marrow by malignant cells. Symptoms include fatigue, pallor, easy bruising and bleeding, fever, and infection; symptoms of extramedullary leukemic infiltration are present in only about 5% of patients. There are a number of subtypes.

A subtype of particular interest is secondary acute myeloid leukemia, referring to the development of AML after myelodysplastic syndromes (MDS) or myeloproliferative neoplasms (MPN). Secondary AML is associated to factors that confer a poor prognosis such as high age and high-risk chromosomal and molecular abnormalities.

Conditioning with Anti-CD117 Antibody for HSC Engraftment

The methods of the invention provide for improved engraftment of stem cells after transplantation into a recipient. The recipient may be immunocompetent, and the transplantation may be performed in the absence of myeloablative conditioning, for example in the absence of radiation and/or chemotherapeutic drugs. The recipient is conditioned with the administration of an effective dose of an antibody specific for CD117.

An effective dose of antibody is the dose that depletes endogenous hematopoietic stem cells. The effective dose will depend on the individual and the specific antibody, but will generally be up to about 100 µg/kg body weight, up to about 250 µg/kg, up to about 500 µg/kg, up to about 750 µg/kg, up to about 1 mg/kg, up to about 1.2 mg/kg, up to about 1.5 mg/kg, up to about 3 mg/kg, up to about 5 mg/kg.

The antibodies are provided in the absence of myeloablative radiation or chemotherapy, may be administered in a single dose, or may be administered twice or more for a period of time sufficient to effect the desired depletion of endogenous stem cells. They may also be administered in combination with other non-myeloablative regimens such as total lymphoid irradiation (TLI) or low dose total body irradiation (TBI). In other embodiments the antibody specific for CD117 is administered in combination with agents that modify or deplete HSC. In other embodiments the antibody specific for CD117 is the only antibody administered. In other embodiments ATG (antithymocyte globulin) is also administered.

The infusion of either bone marrow or peripheral blood stem and progenitor cell (PBPCs) products is a relatively simple process that is performed at the bedside. The stem cell containing product is generally used fresh and is infused through a central vein over a period of several hours. Autologous or allogeneic products may be cryopreserved; if so they are thawed and infused over a specified time period.

Where the donor is allogeneic to the recipient, the HLA type of the donor and recipient may be tested for a match, or haploidentical cells are used. HLA-haploidentical donors can be manipulated by CD34 or CD34CD90 selection. Moreover, HLA-haplo-identical donors are now widely used (and may surpass HLA-identical) for other indications. This widespread use is made possible by the administration of cyclophosphamide in the days post-transplant to prevent GVHD. For HLA matching, traditionally, the loci critical for matching are HLA-A, HLA-B, and HLA-DR. HLA-C and HLA-DQ are also now considered when determining the appropriateness of a donor. A completely matched sibling donor is generally considered the ideal donor. For unrelated donors, a complete match or a single mismatch is considered acceptable for most transplantation, although in certain circumstances, a greater mismatch is tolerated. Preferably matching is both serologic and molecular. Where the donor is umbilical cord blood the degree of tolerable HLA disparity is much greater, and a match of 3-4 out of the 6 HLA-A, HLA-B and HLA-DRB1 antigens is sufficient for transplantation. Immunocompetent donor T cells may be removed using a variety of methods to reduce or eliminate the possibility that graft versus host disease (GVHD) will develop.

For positive selection of CD34$^+$ cells, commercial instruments can be employed to remove the desired cells, using solid-phase, anti-CD34 monoclonal antibodies. With negative selection, anticancer monoclonal antibodies can be used to remove tumor cells, leaving stem cells in the graft.

Conditioning in Combination with Non-Myeloablative Conditioning

In some embodiments, an individual with MDS, or AML, including particularly AML secondary to MDS, is conditioned for HSC engraftment, for example allogeneic HSC engraftment, with a combination of non-myeloablative conditioning, and an effective dose of an antibody specific for CD117. Myelodysplastic syndrome (MDS) disease initiating cells are stem cells that express CD117 at high levels.

Antibodies specific for CD117 effectively deplete MDS HSC. In some embodiments treatment is combined with a non-myeloablative regimen of total lymphoid irradiation (TLI) and anti-thymocyte globulin (ATG), providing for improved disease eradication. In an alternative embodiment, low dose (100-450 cGy) total body irradiation (TBI) is used.

TLI is administered from a photon beam in fractionated doses, usually about daily but the specific schedule may be varied, for a period of time from about 15 days prior to engraftment, about 14 days, about 13 days, about 12 days, about 11 days, about 10 days, and may be from 10 to 15 days prior to engraftment. The total dose of radiation to the major lymphoid organs may be from about 8 Gy to about 12 Gy, with the fractions from about 0.8 Gy to about 1.2 Gy.

Various sources of ATG may be used, for example commercially available sources such as SangStat, Sanofi Genzyme, Fresenius AG, which is generally delivered intravenously, daily, at a dose of from about 1.5 to about 10 mg/kg on consecutive days, e.g. at a dose of from about 1.5 mg/kg to about 2.5 mg/kg, where the administration may take place for about 4 to about 7 days, e.g. around 5 days. The specific schedule may be varied, but generally is initiated from 7 to 12 days prior to engraftment, for example initiating around 11 days prior to engraftment.

As discussed above, the conditioning regimen comprising administration of anti-CD117 antibody, ATG, and TLI are delivered prior to infusion of a donor HSC composition. In some embodiments, the anti-CD117 antibody is delivered at least 10 days prior to HCT infusion, at least 12 days prior to infusion, at least 14 days prior to infusion, and may be about 15 days prior to infusion.

Engraftment of HSC

Following infusion of the conditioning regimen, e.g. anti-CD117 antibody alone or in combination with non-myeloablative conditioning, a population of donor HSC are administered. Administration (transplantation) of the donor HSC may be delayed until the Cmax of the depleting antibody in serum has dropped to a level below about 500 ng/ml, below 100 ng/ml; and may be below about 10 ng/ml; below about 5 ng/ml. The period of time for the drop in antibody titer can be variable depending on the patient; and analysis of antibody levels may be desirable.

Donor cell populations for transplantation are enriched for CD34+ hematopoietic stem cells. In some embodiments the donor cells are HLA-matched. In some embodiments the donor cells are haplotype matched. In some embodiments the donor cells are autologous, including without limitation genetically corrected autologous cells. In some embodiments the donor cells are mobilized peripheral blood cells; in other embodiments the donor cells are bone marrow cells. In some embodiments the donor cells are enriched for expression of CD34, e.g. by art recognized methods such as the cliniMACS® system, by flow cytometry, etc. Cell populations single enriched for CD34 may be from about 50% up to about 90% $CD34^+$ cells. Alternatively cell populations may be tandemly selected for expression of CD34 and CD90, which cell populations may be highly purified, e.g. at least about 85% $CD34^+CD90^+$ cells, at least about 90% $CD34^+CD90^+$ cells, at least about 95% $CD34^+CD90^+$ cells and may be up to about 99% $CD34^+CD90^+$ cells or more. Alternatively unmanipulated bone marrow or mobilized peripheral blood populations are used.

The dose of cells is at least about $2 \times 10^6$ $CD34^+$ cells/kg from a single enriched population, preferably at least about $10 \times 10^6$ $CD34^+$ cells/kg. Higher doses, if available, are generally not deleterious, with the proviso that not more than about $3 \times 10^4$ $CD3^+$ cells/kg are administered. For a tandemly selected population, where a high percentage of the $CD34^+$ cells are HSC, the dose may be lower, e.g. at least about $3 \times 10^5$ $CD34^+$ cells/kg, at least about $5 \times 10^5$ $CD34^+$ cells/kg, at least about $10^6$ $CD34^+$ cells/kg. Higher doses can be administered with the proviso that not more than about $3 \times 10^3$ $CD3^+$ cells/kg are administered.

In some embodiments, success of the procedure is monitored by determining the presence of host-derived myeloid cells, e.g. $CD15^+$ cells, in circulation of the recipient. Blood myeloid chimerism is indicator of true HSC engraftment due to the short-lived nature of myeloid cells. After about 8 weeks post-HCT, methods described herein have provided for measurable and sustained levels of blood myeloid chimerism, e.g. of at least about 1% donor type $CD15^+$ cells, at least about 2% donor type $CD15^+$ cells, at least about 4% donor type $CD15^+$ cells, at least about 8% donor type $CD15^+$ cells, or more. In some embodiments, long term HSC engraftment is evidenced by myeloid chimerism 25% at 24 weeks, reconstitution of T and B lymphoid compartments with reduced or eliminated dependence on immunoglobulin supplementation. Sustained chimerism may be achieved for greater than one year post-transplantation.

Formulations

For depletion the anti-CD117 antibodies are formulated in a pharmaceutical composition. The exact dose will depend on the purpose of the treatment, and will be ascertainable by one skilled in the art using known techniques (e.g., Ansel et al., Pharmaceutical Dosage Forms and Drug Delivery; Ueberman, Pharmaceutical Dosage Forms (vols. 1-3, 1992), Dekker, ISBN 0824770846, 082476918X, 0824712692, 0824716981; Uoyd, The Art, Science and Technology of Pharmaceutical Compounding (1999); and Pickar, Dosage Calculations (1999)). As is known in the art, adjustments for patient condition, systemic versus localized delivery, as well as the age, body weight, general health, sex, diet, time of administration, drug interaction and the severity of the condition may be necessary, and will be ascertainable with routine experimentation by those skilled in the art.

The administration of the agents can be done in a variety of ways as discussed above, including, but not limited to, orally, subcutaneously, intravenously, intranasally, transdermally, intraperitoneally, intramuscularly, intrapulmonary, vaginally, rectally, or intraocularly.

In one embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly useful are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Compositions are administered to a patient in an amount sufficient to substantially deplete targeted endogenous stem cells, as described above. An amount adequate to accomplish this is defined as a "therapeutically effective dose." Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

In the methods of the invention, the agents are administered as a short course of therapy prior to transplantation.

Conditions for Treatment

The indications for stem cell transplantation vary according to disease categories and are influenced by factors such as cytogenetic and/or molecular abnormalities, response to prior therapy, patient age and performance status, disease status (remission vs relapse), disease-specific prognostic factors, availability of a suitable graft source, time of referral, and time to transplant.

Autologous HSCT is currently used to treat the following conditions: Multiple myeloma, Non-Hodgkin lymphoma, Hodgkin disease, Acute myeloid leukemia, Neuroblastoma, Germ cell tumors, Autoimmune disorders—Systemic lupus erythematosus (SLE), systemic sclerosis, Amyloidosis.

Allogenic HSCT is currently used to treat the following disorders: Acute myeloid leukemia, Acute lymphoblastic leukemia, Chronic myeloid leukemia; Chronic lymphocytic leukemia, Myeloproliferative disorders, Myelodysplastic syndromes, Multiple myeloma, Non-Hodgkin lymphoma, Hodgkin disease, Aplastic anemia, Pure red cell aplasia, Paroxysmal nocturnal hemoglobinuria, Fanconi anemia, Thalassemia major, Sickle cell anemia, Severe combined immunodeficiency (SCID), Wiskott-Aldrich syndrome, Hemophagocytic lymphohistiocytosis (HLH), Inborn errors of metabolism e.g. mucopolysaccharidosis, Gaucher disease, metachromatic leukodystrophies, and adrenoleukodystrophies, Epidermolysis bullosa, Severe congenital neutropenia, Shwachman-Diamond syndrome, Diamond-Blackfan anemia, Leukocyte adhesion deficiency, and the like.

Embodiments of the invention include transplantation into a patient suffering from a genetic blood disorder, where exogenous stem cells of a normal phenotype are transplanted into the patient. Such diseases include, without limitation, the treatment of anemias caused by defective hemoglobin synthesis (hemoglobinopathies).

Sickle cell diseases include HbS Disease; drepanocytic anemia; meniscocytosis. Chronic hemolytic anemia occurring almost exclusively in blacks and characterized by sickle-shaped RBCs caused by homozygous inheritance of Hb S. Homozygotes have sickle cell anemia; heterozygotes are not anemic, but the sickling trait (sicklemia) can be demonstrated in vitro. In Hb S, valine is substituted for glutamic acid in the sixth amino acid of the beta chain. Deoxy-Hb S is much less soluble than deoxy-Hb A; it forms a semisolid gel of rodlike tactoids that cause RBCs to sickle at sites of low $PO_2$. Distorted, inflexible RBCs adhere to vascular endothelium and plug small arterioles and capillaries, which leads to occlusion and infarction. Because sickled RBCs are too fragile to withstand the mechanical trauma of circulation, hemolysis occurs after they enter the circulation. In homozygotes, clinical manifestations are caused by anemia and vaso-occlusive events resulting in tissue ischemia and infarction. Growth and development are impaired, and susceptibility to infection increases. Anemia is usually severe but varies highly among patients. Anemia may be exacerbated in children by acute sequestration of sickled cells in the spleen.

Thalassemias are a group of chronic, inherited, microcytic anemias characterized by defective Hb synthesis and ineffective erythropoiesis, particularly common in persons of Mediterranean, African, and Southeast Asian ancestry. Thalassemia is among the most common inherited hemolytic disorders. It results from unbalanced Hb synthesis caused by decreased production of at least one globin polypeptide chain ($\beta$, $\alpha$, $\gamma$, $\delta$).

Aplastic anemia results from a loss of RBC precursors, either from a defect in stem cell pool or an injury to the microenvironment that supports the marrow, and often with borderline high MCV values. The term aplastic anemia commonly implies a panhypoplasia of the marrow with associated leukopenia and thrombocytopenia.

Combined immunodeficiency is a group of disorders characterized by congenital and usually hereditary deficiency of both B- and T-cell systems, lymphoid aplasia, and thymic dysplasia. The combined immunodeficiencies include severe combined immunodeficiency (SCID), Swiss agammaglobulinemia, combined immunodeficiency with adenosine deaminase or nucleoside phosphorylase deficiency, and combined immunodeficiency with immunoglobulins (Nezelof syndrome). Most patients have an early onset of infection with thrush, pneumonia, and diarrhea. If left untreated, most die before age 2. Most patients have profound deficiency of B cells and immunoglobulin. The following are characteristic: lymphopenia, low or absent T-cell levels, poor proliferative response to mitogens, cutaneous anergy, an absent thymic shadow, and diminished lymphoid tissue. Pneumocystis pneumonia and other opportunistic infections are common.

The therapeutic benefit of gene-corrected HSC relies on creation of HSC niche space, and ongoing clinical studies rely on busulfan to achieve gene-correct HSC engraftment. Similar to SCID, transplantation of autologous gene-modified HSC does not require immune ablation of the recipient, and can be achieved with the ablation methods of the disclosure. Indications such as Fanconi anemia and the hemoglobinopathies (sickle cell and thalassemias) can be treated with genetically modified stem cells.

EXPERIMENTAL

Example 1

Successful hematopoietic cell transplantation (HCT) requires emptying hematopoietic stem cell (HSC) niches to permit cell engraftment that can provide life-long donor derived blood formation. Because no alternatives exist, current clinical practice relies on DNA damaging radiation (XRT) or chemotherapy to achieve niche clearance. We have pursued a non-toxic approach to target and deplete HSC with monoclonal antibodies (mAbs) that bind CD117 (cKit). CD117 is a receptor tyrosine kinase expressed on the surface of HSC and early hematopoietic progenitors as well as other non-hematopoietic cells. Ligation of CD117 by its ligand, stem cell factor (SCF), transmits intracellular signals necessary for HSC survival, proliferation and differentiation.

Preclinical studies in lymphocyte deficient mice showed that a single dose of a mAb targeting CD117 results in transient HSC depletion and permits engraftment of purified HSC, proof-of-concept that anti-CD117 mAbs might be used to replace chemoradiation as HCT conditioning. We determined that a humanized anti-human CD117 mAb (AMG 191) depletes human HSC in mice xenografted with human hematopoietic cells, and further, AMG 191 safely depletes endogenous HSC in non-human primates (NHP).

We have opened a phase 1 dose escalation clinical trial to test AMG 191 as the sole conditioning agent for patients undergoing HCT for severe combined immunodeficiency (SCID). The primary endpoint is to assess safety of the antibody, and secondary endpoints that include AMG 191 pharmacokinetics (PK), HSC depletion, hematopoietic recovery, and achievement of donor myeloid chimerism.

SCID is a disorder of diverse genetic cause characterized by profound lymphocyte deficiencies. Because of toxicity concerns, SCID patients transplanted as infants are often infused with donor cell grafts without chemotherapy or XRT conditioning. As a result, subsets of lymphoid progenitors, not HSC, engraft, and although the progenitors generate T and/or natural killer (NK) cells, protective immunity can be poor, and many patients experience negligible B cell function and declining T cell function after several years. Second donor cell "boosts" can be performed but these do not result in HSC engraftment and the immune defects persist.

Here we report preliminary results of the first 2 SCID patients on this trial who underwent a second transplant with AMG 191 as conditioning. Patient (Pt) 1 is a 3-year-old girl with an Artemis gene mutation who received an unconditioned haplo-identical HCT at 7 months of age. She failed to engraft B cells, is intravenous (IV) immunoglobulin (IG) dependent, and has declining T cells. Since her initial HCT, she has experienced chronic and multiply recurrent viral infections. Pt 2 is a 21-year-old man who has SCID presumed due to JAK3 mutation which was determined by genotyping of a similarly affected sibling. At 10 months of age he underwent an unconditioned HCT from an HLA-identical healthy sibling. He failed to engraft B cells, and receives weekly subcutaneous IG injections.

Pts received AMG 191 at the starting dose of 0.1 mg/kg infused IV over 1 hour. PK analysis showed a Cmax range of 2500-2900 ng/ml with linear PK decline. CD34-selected grafts collected from the Pts' original donor were infused when the AMG 191 serum level was below 100 ng/mL. Both Pts tolerated the AMG 191 and donor cell infusion well. In the days and weeks following HCT no clinical aberrations or changes in baseline CBC related to the procedure were observed.

Beginning at 8-wks post-HCT Pt 1 showed evidence of $CD19^+CD20^+$ B cells measured by flow cytometry, which on all prior assessments were negligible. Similarly, at 8-wks, Pt 2 showed increasing $CD19^+CD20^+$ B cells. Extended phenotype analysis showed both Pts were producing increasing numbers of naïve B cells. Chimerism studies confirmed that this surge in B cells were donor derived. Moreover, for both Pts, blood myeloid chimerism measured by Short Tandem Repeat (STR) analysis of stringently sorted $CD15^+$ cells rose from 0% pre-HCT to 5% and 9% for Pts 1 and 2, respectively at 8-wks post-HCT.

The Table shows results of sorted donor $CD15^+$ cell chimerism relative to time of transplant, as well as $CD19^+$ cell chimerism and absolute number of $CD19^+$ cells obtained by standard clinical laboratory methods.

Conclusion: Early clinical data suggest that AMG 191 can safely clear HSC niche space and permit engraftment of HSC in patients with SCID.

| Blood CD15+ and CD19+ Chimerism, and Absolute CD19+ Cell Values | | | | | | |
|---|---|---|---|---|---|---|
| Time relative to HCT | Pt #1 - Sorted Blood CD15 Chimerism* (% donor) | Pt #2 - Sorted Blood CD15 Chimerism* (% donor) | Pt #1 - Blood CD19† Chimerism† (% donor) | Pt #2 - Blood CD19 Chimerism† (% donor) | Pt #1 - Blood Absolute CD19 (K/ul) | Pt #2 - Blood Absolute CD19 (K/ul) |
| Pre | 0% | 0% | 4% | 10% | 0% | 0 |
| Wk 4 | 0% | 1% | 9% | ND | 0% | 0 |
| Wk 8 | 5% | 9% | 70% | 26% | 15 K/uL | 12 K/uL |

| Blood CD15+ and CD19+ Chimerism, and Absolute CD19+ Cell Values | | | | | | |
|---|---|---|---|---|---|---|
| Time relative to HCT | Pt #1 - Sorted Blood CD15 Chimerism* (% donor) | Pt #2 - Sorted Blood CD15 Chimerism* (% donor) | Pt #1 - Blood CD19 Chimerism† (% donor) | Pt #2 - Blood CD19 Chimerism† (% donor) | Pt #1 - Blood Absolute CD19 (K/ul) | Pt #2 - Blood Absolute CD19 (K/ul) |
| Wk 12 | 5% | 10 | 75% | Too early | 11 K/uL | Too early |
| Wk 18 | 4% | Too early | 51% | Too early | 22 K/uL | Too early |

*Flow cytometry sorted CD15+ cells analyzed by STR
†Magnetic bead sorted CD19+ cells analyzed by STR. Purity not assessed due to low cell numbers.

Example 2

An Antibody Against CD117 can Enable Hematopoietic Stem Cell Engraftment in Patients Undergoing Transplantation Successful hematopoietic cell transplantation (HCT) requires emptying hematopoietic stem cell (HSC) niches to permit HSC engraftment. Currently HCT relies on DNA damaging radiation (XRT) or chemotherapy to achieve niche clearance. We have pursued a non-toxic approach to target and deplete HSC with monoclonal antibodies (mAbs) that bind CD117 (cKit). CD117 is a receptor tyrosine kinase expressed on the surface of HSC and progenitors. Ligation of CD117 by stem cell factor (SCF) transmits signals for HSC survival, proliferation and differentiation. We determined that a humanized anti-CD117 mAb (AMG 191) depletes human HSC in mice xenografted with human cells and safely depletes HSC of non-human primates (NHP).

Here we report early results from our phase 1 dose escalation trial which tests AMG 191 as the sole conditioning agent for patients undergoing HCT for severe combined immunodeficiency (SCID). SCID is a genetic disorder of profound lymphocyte deficiencies curable only by HCT. Because of toxicity concerns, SCID infants often receive donor HSC graft infusion without conditioning. As a result, progenitors, but not HSC, engraft, which can generate life-saving T cells. However, immunity can be poor, and some suffer poor B cell and/or T cell reconstitution. Second donor cell "boosts" generally do not result in HSC engraftment, and immune defects can persist.

The primary endpoint of the trial is safety of AMG 191, and secondary endpoints include AMG 191 pharmacokinetics (PK), host HSC depletion, donor hematopoietic recovery, and achievement of donor myeloid chimerism. Two patients (Pt) with T-B-NK+ SCID underwent second HCT with AMG 191. Both had prior unconditioned HCT as infants, failed to engraft B cells and remain dependent on immunoglobulin. AMG 191 was infused at the lowest dose (0.1 mg/kg). PK analyses showed a Cmax of 2500-2900 ng/ml and linear elimination. CD34-selected grafts from the original donors were infused when the AMG 191 serum level was <100 ng/mL. Following HCT, no clinical aberrations or significant changes in baseline CBC related to the HCT were observed.

For both Pts, blood myeloid chimerism, the indicator of true HSC engraftment, rose from 0% pre-HCT to measurable and sustained levels (Table 1) beginning at 8-wks post-HCT. Also at 8-wks, both Pts showed evidence of increasing CD19+CD20+ B cells. Extended phenotype analysis showed that naïve B cells were present and chimerism studies confirmed that the observed B cells were donor derived. These data are the first to show that a mAb targeting CD117 can safely clear HSC niche space and permit engraftment of HSC with multilineage reconstitution in patients undergoing HCT.

TABLE 1

| Sorted Blood CD15+ Cell Chimerism (% donor)† | | |
|---|---|---|
| Time relative to HCT | Pt #1 | Pt #2 |
| Pre | 0% | 0% |
| Wk 4 | 0% | 1% |
| Wk 8 | 5% | 9% |
| Wk 12 | 5% | 10% |
| Wk 18 | 4% | Pending‡ |
| Wk 24 | 7% | Pending‡ |

†Analyzed by STR, unmonitored data.
‡Time point not reached

Example 3

A fundamental requirement for a successful BMT is the life-long engraftment of recipients with replacement hematopoietic stem cells (HSC). Achievement of durable HSC engraftment involves multiple factors including the recipient conditioning regimen, the nature of the genetic disparity between donor and recipient, and the content of the hematopoietic graft. Animal and clinical studies have shown that the biology of host resistance is complex, involving both immune and non-immune elements. The primary immune mediators of allogeneic HSC resistance are T lymphocytes and NK cells. This application focuses on the non-immune barriers to HSC engraftment which apply to both allogeneic or autologous gene corrected HSC. At present, in clinical practice, the only method for overcoming this non-immune barrier is to treat recipients with toxic DNA-damaging chemotherapy (i.e., busulfan, melphalan) or radiation.

An anti-CD117 mAb (AMG 191) that specifically depletes endogenous HSC with minimal off-target toxicity is used to replace chemoradiation in overcoming the non-immune engraftment barrier. Currently, no such reagent is used to prepare patients for transplant. The rationale for this approach is based on our understanding of the biology of the host barrier cells that resist HSC engraftment. The development of AMG 191 for the purpose of HCT conditioning is based on studies first performed in mice followed by translation of this work to an open clinical trial which tests if AMG 191 used as the sole conditioning agent for children with SCID permits engraftment of donor HSC. Key preclinical studies performed by us supporting the open IND are in vitro mouse and human cell experiments, and in vivo studies performed in mice xenografted with human hematopoietic cells and in the large animal model of non-human primates (NHP). In addition, there were two first-in-human safety studies in healthy volunteers which supported the ongoing trial. Remarkably, we observe both safety and efficacy of AMG 191 as a single transplant conditioning agent in children with SCID undergoing allogeneic HCT.

SCID is the most deleterious of the congenital primary immune disorders. It is a rare disease of diverse genetic causes characterized by profound deficiencies in lymphocyte numbers and function. T cells are the most important and severely affected lymphocyte population, although in certain forms of SCID, B and NK cells are also reduced and/or dysfunctional. Progressive infections lead to fatality early in life unless immune reconstitution is accomplished, and most untreated infants die before the age of two. Allogeneic HCT is the only proven cure for SCID and has been the standard of care for decades.

Despite its rarity, treatment of SCID has played a central role in the development and evolution of the HCT field. Because most SCID patients do not have an HLA-matched sibling donor and the critical need to generate immunity, HCT for SCID led the way for using unrelated donors and partially HLA-matched (haploidentical) related donors. SCID patients were also the first to be successfully transplanted with T cell depleted grafts and genetically corrected autologous grafts. Fundamental insights into the biology of HCT learned first from HCT of SCID include: the importance of donor T cells as causative of GVHD; that transplant success relies in part on infusion of large number of HSCs relative to patient size; and immune competent donor cells can cause the marrow aplasia.

The unique biology of SCID, as well as the transplant community's prior experience addressing the needs of SCID patients make them the ideal target population to test the ability of an anti-CD117 mAb to safely permit engraftment of purified allogeneic HSC: (1) Due to profound immune deficiency in newly diagnosed SCID patients and in those previously transplanted SCID patients with poor graft function and who are tolerant to their original donor, the effects of the mAb on facilitating HSC engraftment will not be obscured by immune rejection. (2) Extensive experience with SCID patients transplanted in the absence of conditioning allows objective measurement if the anti-CD117 mAb improves engraftment. (3) Transplantation of purified human HSC minimize the syndromes of acute and subacute GVHD which remain problematic following haploidentical AHCT of SCID patients, despite T cell depletion.

SCID patients are provided with a safer, more effective and better-tolerated approach to HCT. Treatment of these patients will lead the way to a better therapy that will benefit all patients for whom allogeneic HCT is currently needed and open the door to allogeneic HSC transplantation for other indications including the treatment of severe autoimmune diseases and the induction of donor specific tolerance to transplanted organs.

Preclinical Background Studies

Depletion of host HSC is required for engraftment by replacement HSC. Children with SCID lack the immune capability to reject allografts, yet fail to engraft with donor HSC unless myeloablative conditioning is applied. Preclinical studies support the idea that the identify of this marrow space barrier resident host HSC that firmly occupy specialized niches within the marrow, and unless these HSC are unseated, donor engraftment will either not occur or occur at a minimal level.

Studies in mice showed that in normal and immune deficient animals most HSC niches are occupied, and only a small number of niches are readily available for transplanted HSCs. In these studies blood granulocyte chimerism was used as the surrogate measure of donor HSC chimerism. Infusion of unconditioned immune deficient RAG2$^{-/-}$γc$^{-/-}$ mice that lack all lymphoid cells (T, B, NK) with increasing numbers of purified gene-marked congenic HSC showed that donor chimerism increased measurably at doses between 10 to 250 HSC per mouse, but transplantation of >250 HSC led to negligible changes in chimerism. These data suggest that without conditioning, HSC engraftment is limited by the number of saturable niches that are empty at the time of transplant or become available during the narrow window during which infused HSC maintain viability and pluripotency outside the niche.

To determine if specific elimination of host HSC would permit high levels of donor HSC engraftment, antibodies against several candidate target molecules expressed on HSC were tested. ACK2, an rat-anti-mouse IgG2b mAb that targets CD117 was selected. CD117 also known as c-Kit is the receptor for stem cell factor (SCF). In vivo administration of ACK2 to T- and B-cell deficient Rag2$^{-/-}$ mice, resulted in dramatic depletion of host HSC, resulting in a 98% decrease in phenotypic and functional endogenous HSC in mouse marrow. The reduction in HSC was only transient and two weeks post-administration of ACK2, endogenous HSC fully recovered. Transplantation of donor HSC immediately after administration of the mAb resulted in donor cell elimination. Pharmacokinetic analysis revealed that ACK2 cleared from the serum in ~7-9 days, suggesting a window of time when the HSC niches could be available. Infusion of congenic HSC at day 9 post-ACK2 resulted in long-term donor derived engraftment of up to 90% (depending on HSC cell dose) as indicated by donor granulocyte chimerism. The increased chimerism was highly significant compared to unconditioned hosts, which engrafted at <1%. Importantly, recipient mice showed no apparent side effects from the ACK2 treatment other than transient graying of their fur, as c-Kit is also expressed on melanocytes. Normal marrow composition was restored within two weeks after ACK2 injection and peripheral blood counts were not adversely affected.

In Vitro and Non-Human Primate Studies

Anti-human CD117 mAbs SR-1 and AMG 191 demonstrate anti-HSC activity in vitro and in vivo. Translating this approach to clinical use identified anti-human CD117 (anti-hCD117) mAbs with similar activity in vitro and in vivo to ACK2. We produced and surveyed several mouse anti-hCD117 mAbs, and determined that clone SR-1 binds to and uniquely inhibits binding of SCF to CD117. A clinical grade humanized anti-hCD117 mAb designated AMG 191 was developed by Amgen. Like SR-1, AMG 191 blocks SCF binding to CD117 thereby interrupting the signals transmitted through this receptor.

Figure 2:
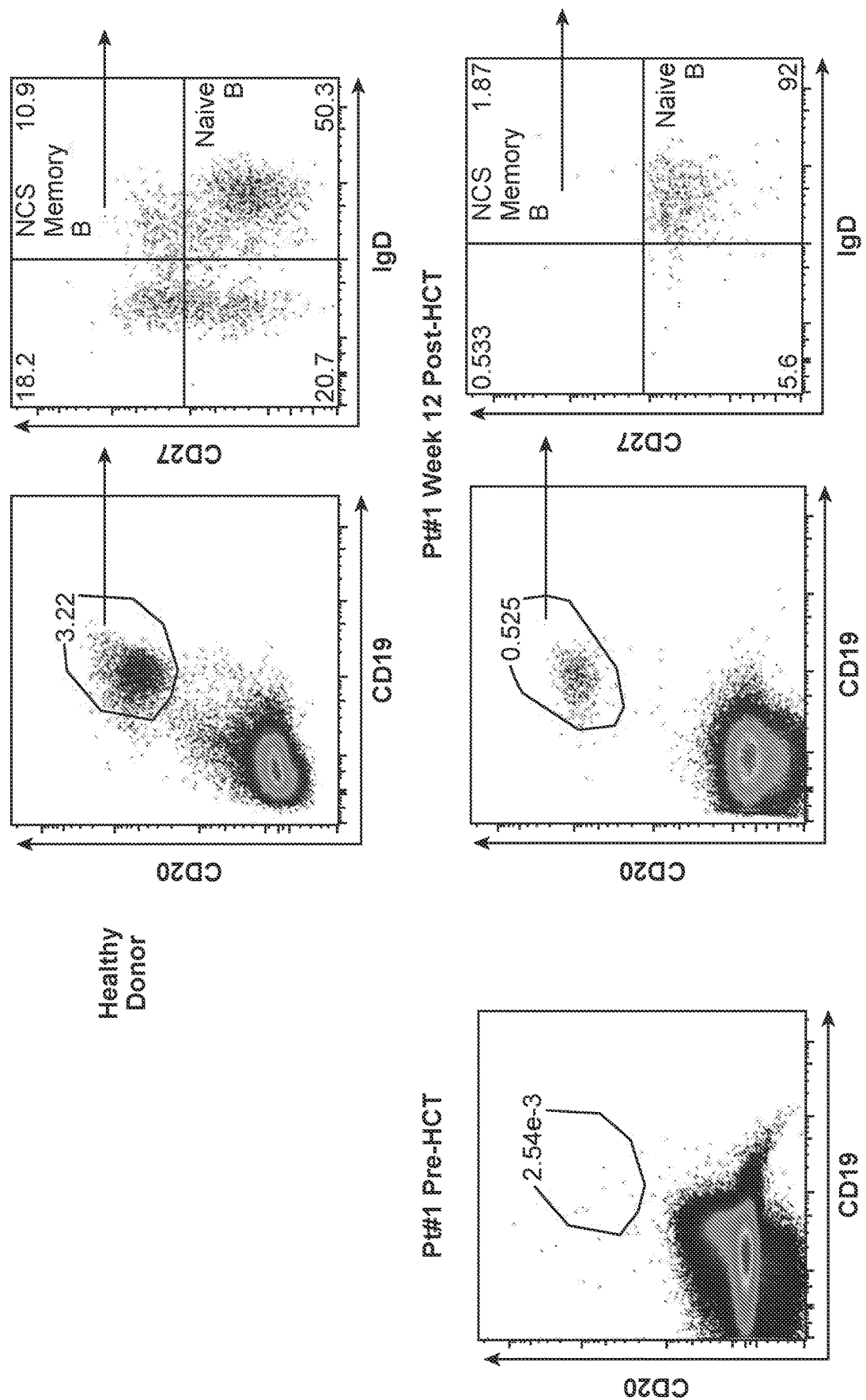
FIG. 2. Patient blood analysis. Peripheral blood samples were obtained from health control or Patient #1 at 12 weeks following transplant using AMG 191 as sole conditioning and infusion of CD34+-enriched donor mobilized peripheral cells. White blood cells were stained with the B cell markers CD19 and CD20, and analyzed on the fluorescent activated cell sorter. Extended B cell phenotype studies were performed using staining for CD27 and IgD. The figure shows that pre-transplant Patient #1 had no B cell peripheral in the blood. Whereas 12 weeks post-transplant CD19+CD20+ B cells are present, and most are of the naïve phenotype, suggesting that B cells are being generated from progenitor cells.
Figure 3A:
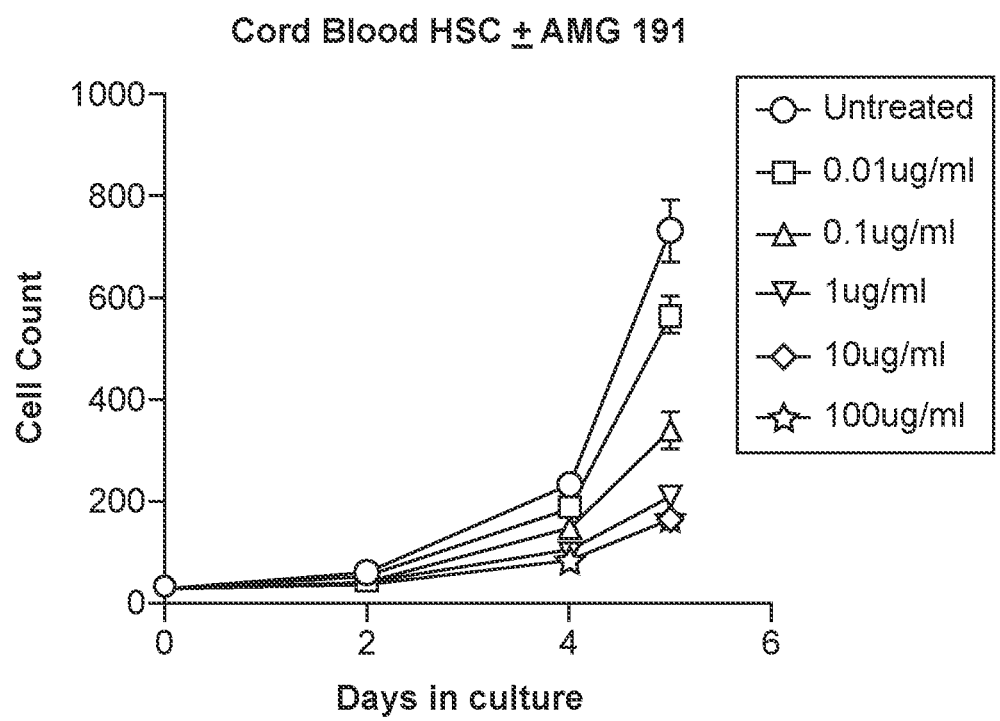
FIGS. 3A-3B.
Figure 3B:
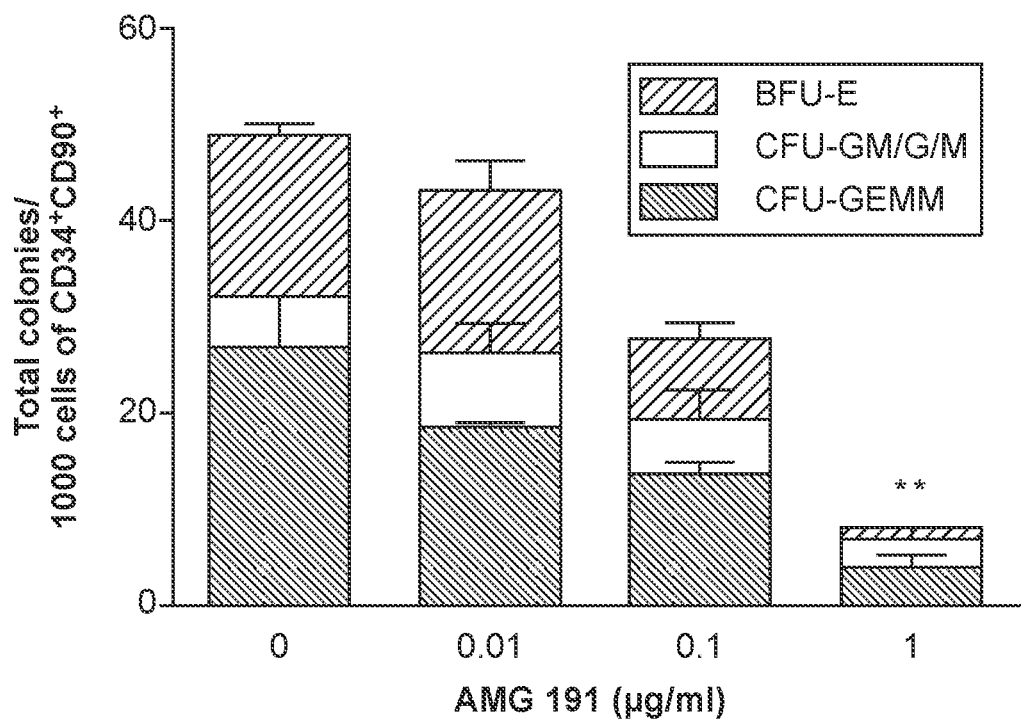

We performed a series of in vitro and in vivo studies which demonstrated that both AMG 191 and SR-1 have activity against HSPC. Here we summarize our studies on AMG 191. To assess AMG 191 for its ability to functionally inhibit hematopoietic activity of human HSCs in vitro, HSC proliferation and colony forming assay were performed. AMG 191 demonstrated inhibition of human BM HSC proliferation in a dose dependent manner (FIG. 3A), similar to the mouse anti-CD117 mAb. AMG 191 also markedly reduced the colony formation of erythroid progenitors (BFU-E) and multi-potential granulocyte, erythroid, macrophage and megakaryocyte progenitors (CFU-GEMM) from FACS-purified human CD34$^+$CD90$^+$ HSC (FIG. 3B). Lesser inhibitory effects of AMG 191 were noted on the more downstream granulocyte and macrophage progenitors (CFU-GM/G/M). The inhibitory effect of AMG 191 on the formation of CFU-GEMM, the more primitive progenitors and mixed colonies, suggests that AMG 191 suppresses the proliferation and/or differentiation of CD34+CD90+ HSCs to lineage-committed hematopoietic progenitors in vitro by inhibiting SCF binding. The impairment of BFU-E colony formation by AMG 191 is consistent with the expression and function of CD117 on erythroid progenitors.

Figure 4A:
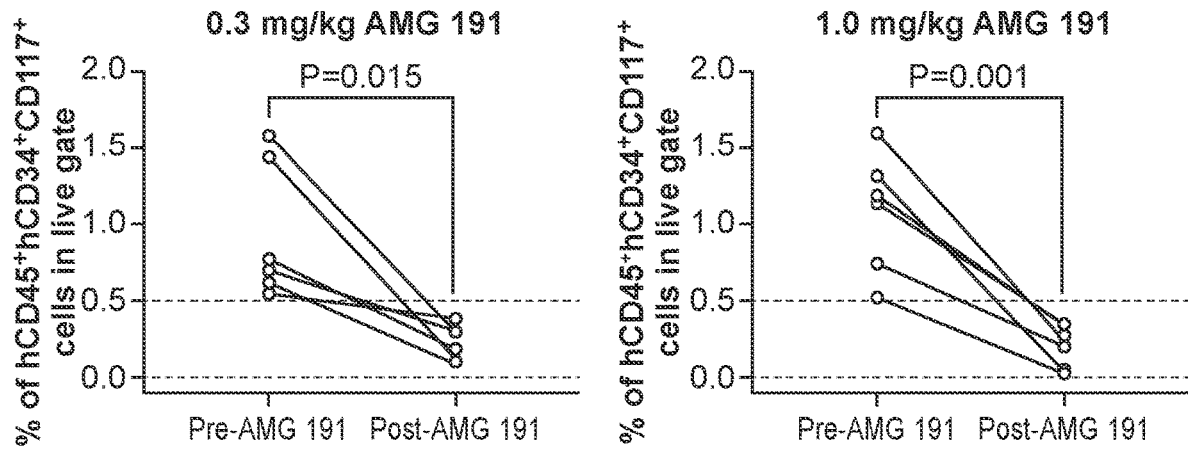
FIGS. 4A-4B.

We then examined if AMG 191 can safely and effectively deplete human HSPCs in vivo and permit engraftment of human donor hematopoietic cells by utilizing the xenograft model of human HSPC engrafted mice[43]. Immune deficient NOD SCID gamma (NSG) mice which were stably engrafted with human cord blood CD34+ cells (humanized NSG)[44] were treated with 0.3 and 1.0 mg/kg of AMG 191 via a single IV injection. The effect of AMG 191 on human cells was assessed by BM aspirates two-weeks post AMG 191 injection. Depletion of human HSPCs was observed in all humanized mice treated with AMG 191 (FIG. 4A). The ratios of human CD45+ (hCD45+)/mouse CD45+ (mCD45+) cells in the BM decreased in most mice treated with AMG 191, consistent with preferential depletion of engrafted human cells by this antibody compared to endogenous mouse cells.

Figure 4B:
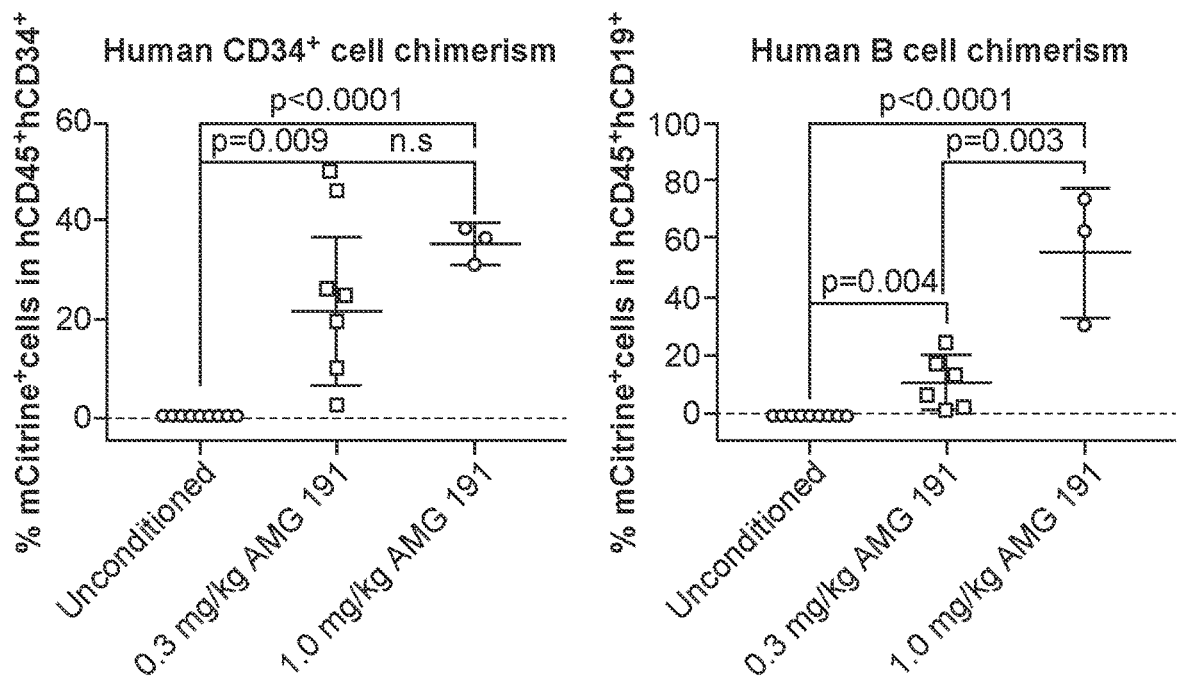

We next studied in stably human-xenografted mice if HSPC depletion by AMG 191 could permit engraftment of a second donor human HSC graft thereby modeling an allogeneic HCT. To distinguish cells from the first and second human donors in the humanized NSG recipients, the second human graft was transduced with mCitrine expressing lentivirus. Transduced CD34+ cells were transplanted into humanized NSG mice treated with 0.3 or 1.0 mg/kg AMG 191. Control humanized NSG mice did not receive AMG 191. Transplant days were selected based on PK studies of AMG 191 performed on the mice that received 1.0 mg/kg. Second donor grafts were infused on days 21 and 25 post AMG 191, days when the PK level was predicted to fall below 2000 ng/ml. The choice of this threshold level was based on PK studies in mice which showed that serum levels <2200 ng/ml of the anti-mouse CD117 mAb had no effect on donor mouse HSC engraftment. Engraftment of the gene marked second human donor cells among hCD45+hCD34+ and hCD45+hCD19+ cells was observed in all mice treated with AMG 191, whereas no evidence of second donor chimerism was found in unconditioned mice, suggesting that AMG 191 permitted second donor HSPC engraftment. Donor chimerism was enhanced in mice treated with 1.0 mg/kg AMG 191 compared to the 0.3 mg/kg dose, suggesting a beneficial effect of a higher dose of AMG 191 on second donor engraftment (FIG. 4B). Taken together, these data demonstrate that AMG 191 depletes human HSPCs and that this depletion permits engraftment of second human progenitor cells in humanized mice.

Figure 5:
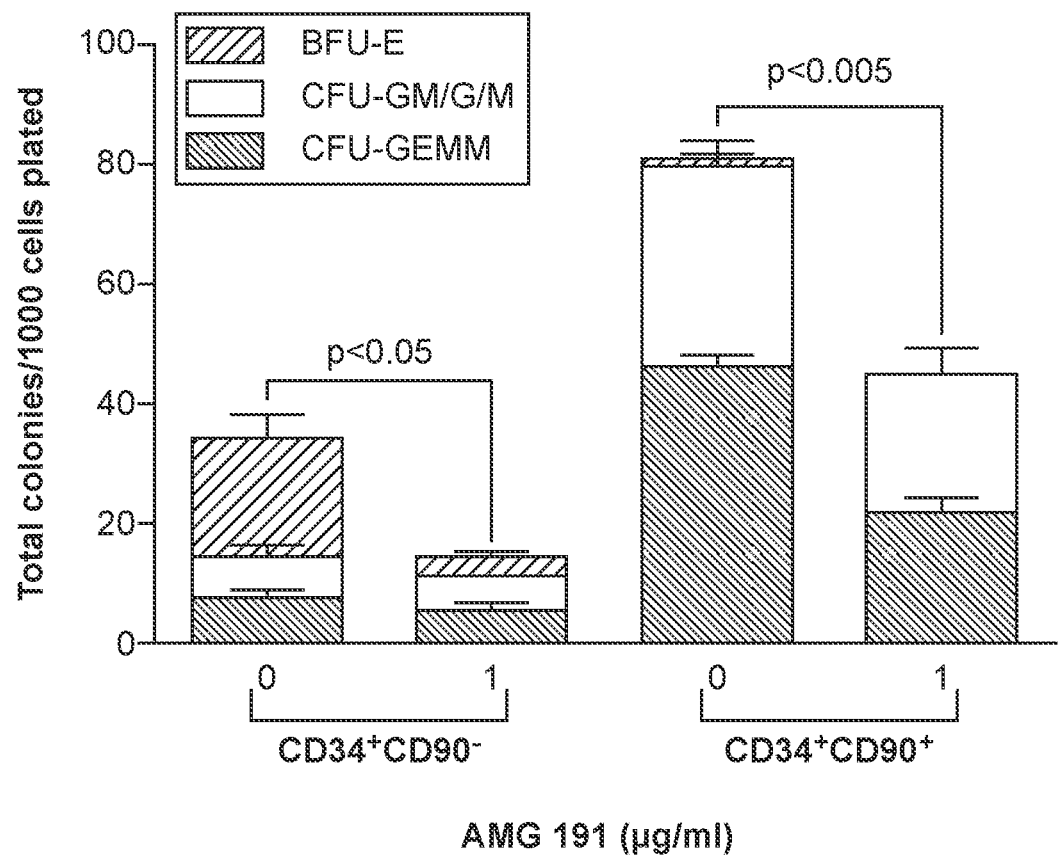
FIG. 5: AMG 191 inhibits hematopoiesis of NHP CD34+ CD90− and CD34+CD90+ cells. $10^3$ of each CD34+CD90+ and CD34+CD90− cells were sorted from NHP BM aspirates and cultured in methylcellulose media without or with AMG 191 (1 μg/ml). Untreated vs AMG 191 treated in CD34+CD90− cells, total colony and BFU-E, p<0.05, Untreated vs AMG 191 treated in CD34+CD90+ cells, total colony and CFU-GEMM, p<0.005. Data and error bars represent the mean±sem.

AMG 191 suppresses non-human primate (NHP) hematopoiesis in vitro. The effect of AMG 191 on hematopoiesis was next tested in a large animal model, non-human primates (cynomolgus macaques). We first identified that AMG 191's binds to CD34+CD90+ NHP HSC and then tested its ability to functionally inhibit NHP hematopoietic activity (FIG. 5). Colony forming unit (CFU) assays were performed in the presence or absence of AMG 191 on purified CD34+CD90+ and CD34+CD90+ cells isolated from the BM of NHP. Similar to its inhibitory effect on human HSPC colony formation, AMG 191 impaired the formation of BFU-E and CFU-GEMM colonies from purified NHP CD34+CD90− and CD34+CD90+ cells but had less effect on the formation of the more differentiated CFU-GM/G/M colonies. CD34+CD90+ cells from NHP BM formed few BFU-E compared to CFU-GEMM. That BFU-E rarely arise from the more primitive NHP HSPC has also been reported in the pig-tailed macaque model. These data show that AMG 191 targets NHP HSCs and suppresses their hematopoietic activities in vitro.

Figure 6A:
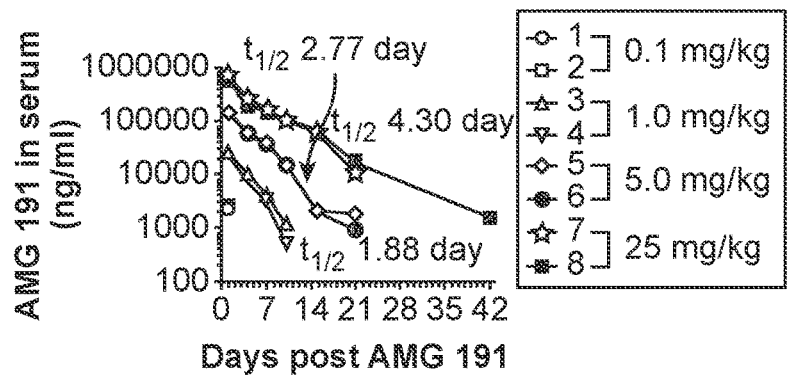
FIGS. 6A-6D: In vivo effect of AMG 191 on CD34+ HSPCs and blood of NHP.
Figure 6B:
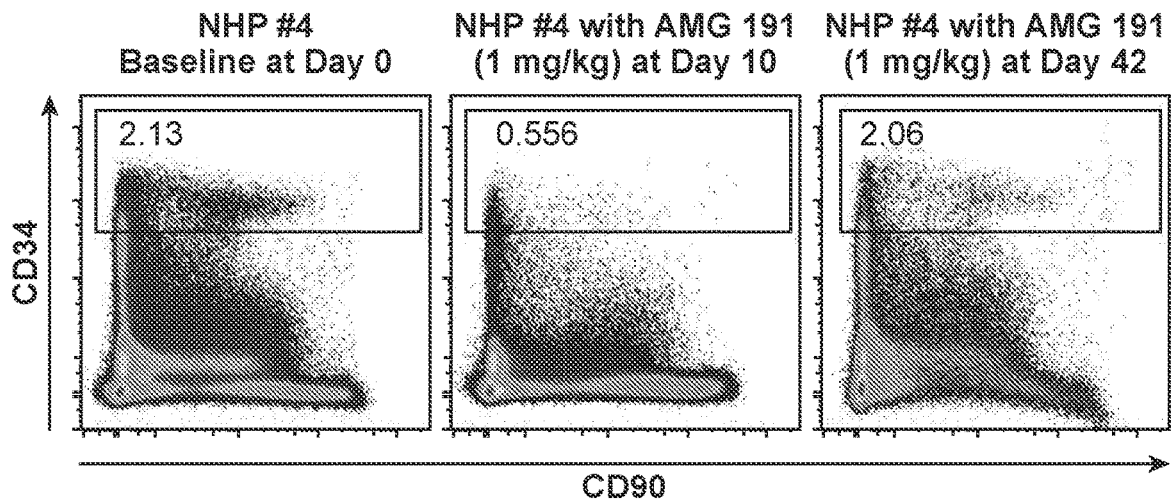
Figure 6C:
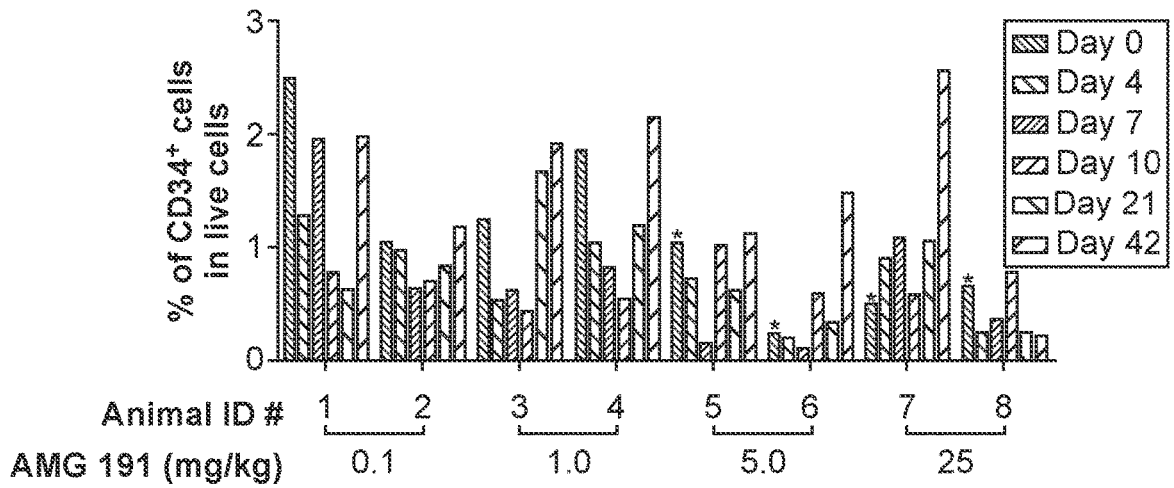

AMG 191 depletes CD34+ HSPCs in BM of NHP. The HSPC depletive in vivo activity of AMG 191 was then tested in NHP (FIG. 6). Immunocompetent juvenile NHP received a single IV infusion of AMG 191 (0.1, 1, 5, or 25 mg/kg). All animals survived to the end of study and there were no adverse clinical observations attributable to treatment with AMG 191. The pharmacokinetic (PK) clearance of AMG 191 in the serum was dose dependent in a nonlinear fashion (FIG. 6A). Phenotypic CD34+ HSPCs were depleted in the BM of all animals that received AMG 191 except NHP #7 (FIG. 6B-C). Of note, at the time of infusion, NHP #7 had emesis, markedly elevated neutrophils and white blood cells (WBCs) suggesting that it was ill which may have been influenced this animal's physiologic state. HSPC depletion lasted up to 21 days in most animals and >42 days in NHP #8, which received the highest dose. All animals except NHP #8 recovered normal range HSPC frequency by day 42, suggesting that high doses of AMG 191 can cause delayed HSPC recovery.

Figure 6D:
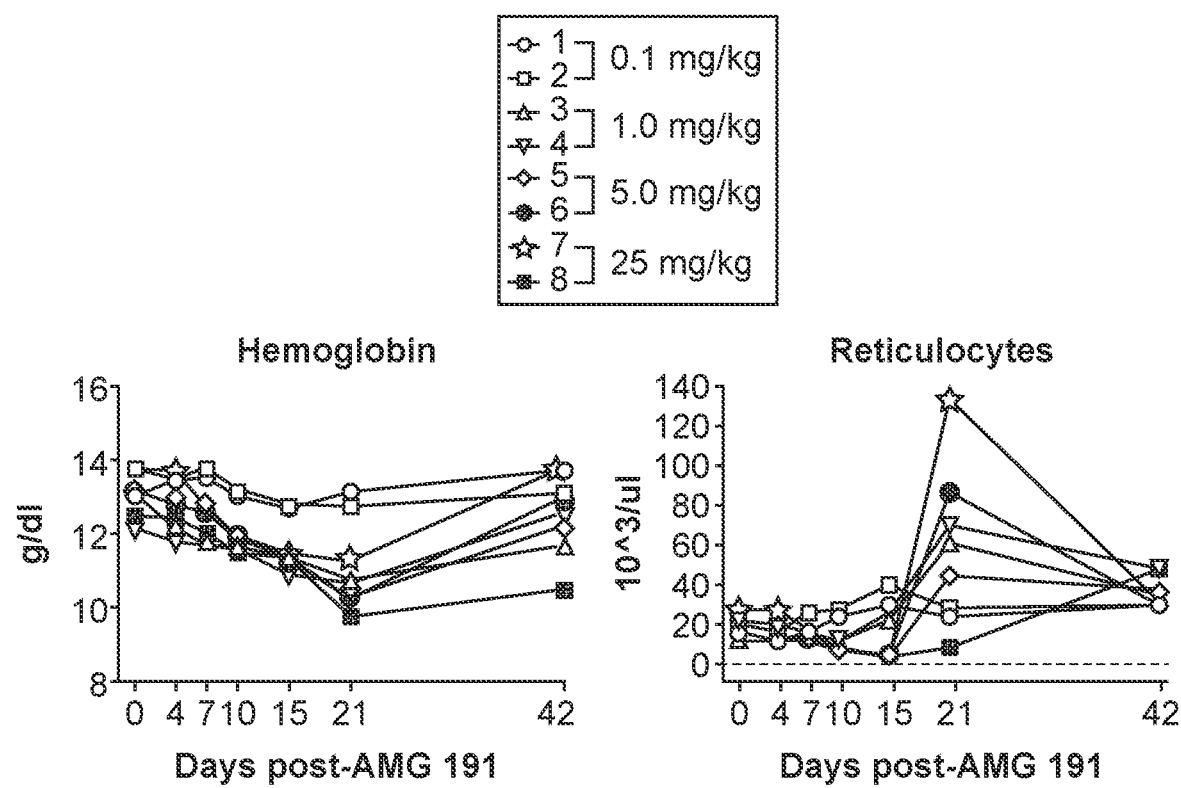

Depletion of HSPCs in NHP BM as assessed by phenotype studies correlated with functional studies that showed reduced progenitor colony formation. CD117 is highly expressed on HSPC, as well as early myeloid progenitor cells and downstream erythroid lineage cells. Its expression is also restricted to a small subset of NK and early T cell precursors. Peripheral blood measurements showed that, as expected based on the expression pattern, the red blood cell (RBC) lineage was most impacted by AMG 191. In all animals except NHP #1-2 that received the lowest dose, significant reductions in hemoglobins were noted, which nadired at day 21 and then trended upward with most animals recovering to baseline by day 42 (FIG. 6D). Similarly, reticulocyte counts in peripheral blood, a measure of red cell production, were decreased in NHPs #3-8. Interestingly, at day 21, the reticulocyte counts rebounded to levels above baseline in most animals receiving the higher AMG 191 doses (NHP #8 excepted) and returned to baseline by day 42. Because hematopoiesis is sensitive to RBC loss, we interpret this transient reticulocytosis to reflect endogenous erythropoietic response elicited by the AMG 191-induced transient anemia. Again, NHP #8, which received the highest dose, demonstrated persistently low hemoglobin and reticulocytes levels at day 21, which trended towards recovery by day 42 (FIG. 6A, 6D).

Clincal Studies

Phase 1 Clinical Study Testing AMG 191 as Transplant Conditioning for SCID.

Study Design. In this study AMG 191 is delivered as a one-time IV dose which is followed by infusion of donor HSC when the antibody has sufficiently been cleared from the serum (<100 ng/mL). It is a 3+3 dose escalation study with dose levels of AMG 191 of 0.1, 0.3, 1.0 mg/kg. These doses were determined based upon the in vivo NHP studies performed by us, which showed safety at all doses up to 25 mg/kg, and effective clearance of NHP HSC from the BM at doses as low as 0.1 mg/kg. The maximum dose of 1 mg/kg is roughly 3-5 times lower than the maximum dose that was administered SC to healthy volunteers. The primary endpoint is to assess the safety and tolerability of AMG 191. Secondary endpoints include AMG 191 PK, host HSC depletion, and determination of the AMG 191 dose that achieves adequate donor HSC engraftment, defined as >5% donor granulocyte chimerism at 24 weeks.

Figure 7:
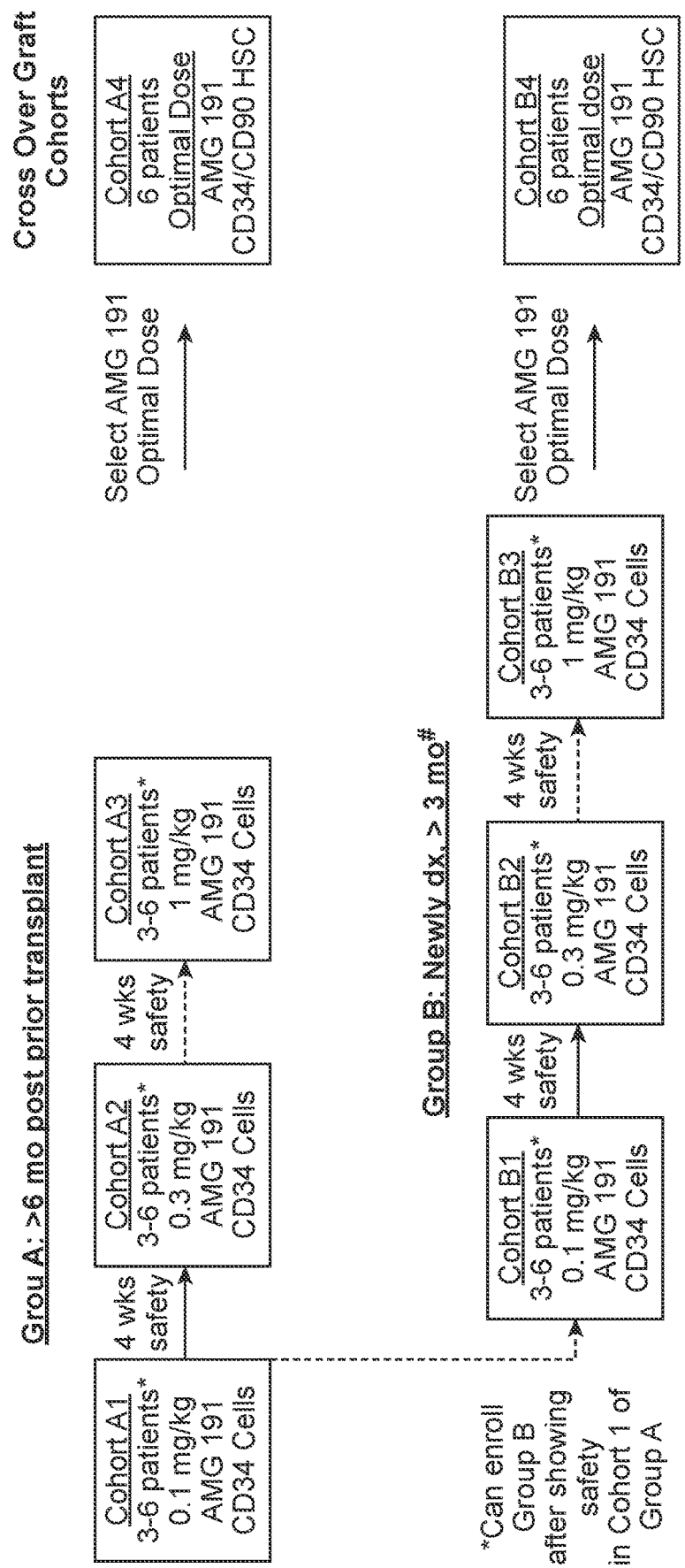
FIG. 7: Transplant enrollment Schema. The study design is outlined in Trial Enrollment Schema. The study will enroll two groups of SCID patients in staggered order. There will be 3 initial patients enrolled in each dose cohort, with 1 sentinel patient. The first patient will be followed for 4 weeks post-transplant for safety monitoring before commencing dosing of the next patients. Group A will enroll patients ≥6 months of age who have previously undergone an allogeneic HCT but have low-level donor engraftment and inadequate T and/or B cell function as defined by specific criteria. Group B will enroll patients a 3 months of age with newly diagnosed SCID. Group B will commence enrollment after the first dose cohort of Group A (A1) has demonstrated safety at four weeks post-transplant. The Optimal AMG 191 Dose is defined as the lowest safe and tolerable dose that achieves the highest level of engraftment of CD34$^+$ cells at Week 24, based on an assessment of the totality of data from all Cohorts and agreement by the DSMC.

The study design (FIG. 7) enrolls two groups of SCID patients in staggered order based on prior HCT status. Group A are patients who have had prior allogeneic HCT but poor immune function. Group B are patients a 3 months of age with newly diagnosed SCID. Group B, opened for enrollment after the first dose cohort of Group A (A1) demonstrated safety at four weeks post-HCT. The rationale for this design, which was favorably viewed by the FDA, is based on demonstration of safety, assessment of PK, and correlation of PK with pharmacodynamics (PD) in older patients who have undergone an HCT with suboptimal immune function before extending to transplant-naïve infants.

We have completed the first dose cohort (A1) and treated the first two patient in the second dose cohort (A2). All five patients tolerated the AMG 191 infusion and the subsequent infusion of their CD34-selected donor cells without clinical problems. In fact, the patients have done so well, the treating clinicians are inquiring about making the procedure an outpatient one. Characteristics of the five patients treated to date are shown in Table 2. The patients are a mix of different SCID genotypes. All patients had prior HCT as infants, and failed to engraft with HSC as evidenced by 0% myeloid chimerism, the indicator of true HSC engraftment (Table 3). All have no or very low levels of B cells and remain immunoglobulin dependent. Patient (Pt) #1 was clinically frail with history of chronic infections and diarrhea, and poor T cell levels. Pt #2 is clinically stable but remains on life-long exogenous immunoglobulin which he injects SC. As a consequence his abdomen is scarred by the these injections, and as he is now an adult, insurance coverage for this essential therapy is uncertain. Prior to participation in this trial: Pt #3 was clinically fragile, had poor T cell levels. He has had chronic infections, diarrhea and is malnourished. Although 13 years old he weighed 12 Kg; Pt #4 was clinically stable but had poor T cell function and suffered from recurrent sinus infections. Pt #5 was clinically stable but failed to engraft B cells and had waning T cell immunity. Initial patients at 52 weeks had sustained chimerism at detectable levels.

Figure 8:
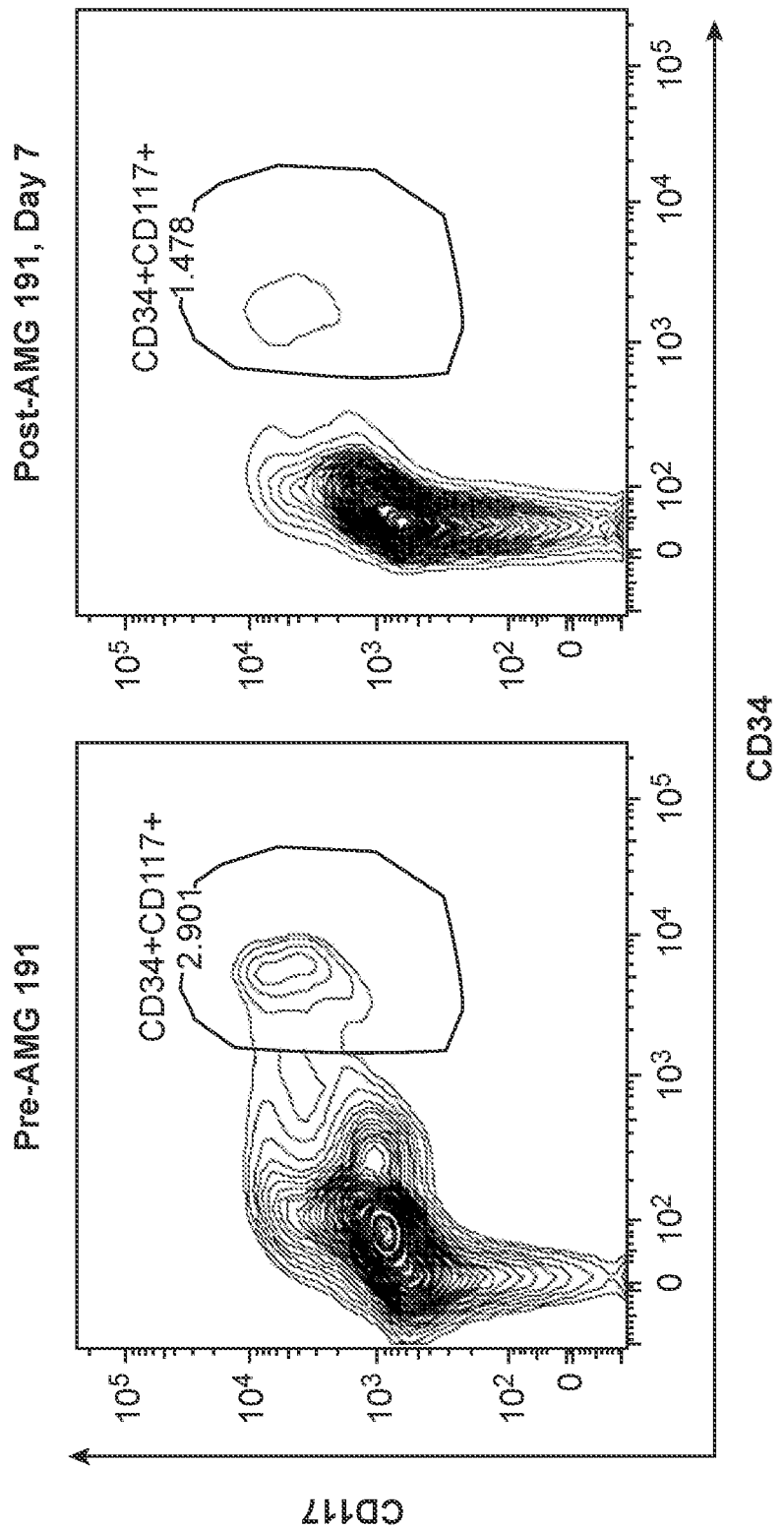
FIG. 8: Depletion of HSC in BM of Pt #2. HSCs are stained and analyzed by FACS using markers CD34 and CD117 from bone marrow obtained pre- and 7 days post-AMG 191 infusion. The anti-CD117 labeled antibody use to identify this population binds a non-cross blocking epitope with AMG 191.

To assess for host HSC depletion by AMG 191, patients who consented (n=3) underwent BM aspiration pre-AMG 191 and on the day of donor cell infusion. All patients showed evidence of HSC depletion on their BM as determined by staining for HSC. FIG. 8 shows a representative staining profile for CD117$^+$CD34$^+$ cells. CD117 is stained with a non-crossblocking mAb. BMs were also asses by CD38 and CD90 stains to confirm HSC depletion.

Figure 9B:
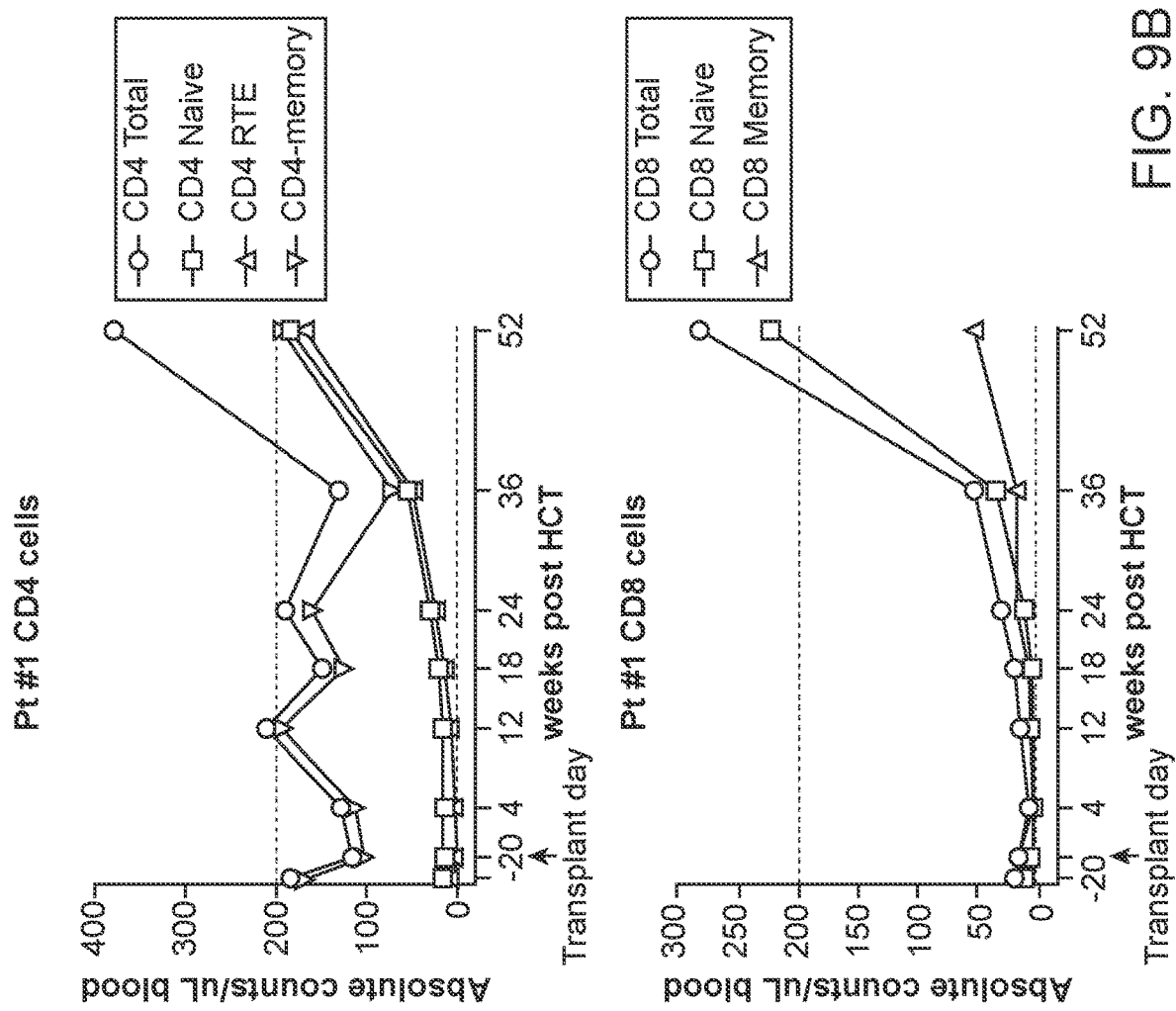
Figure 10:
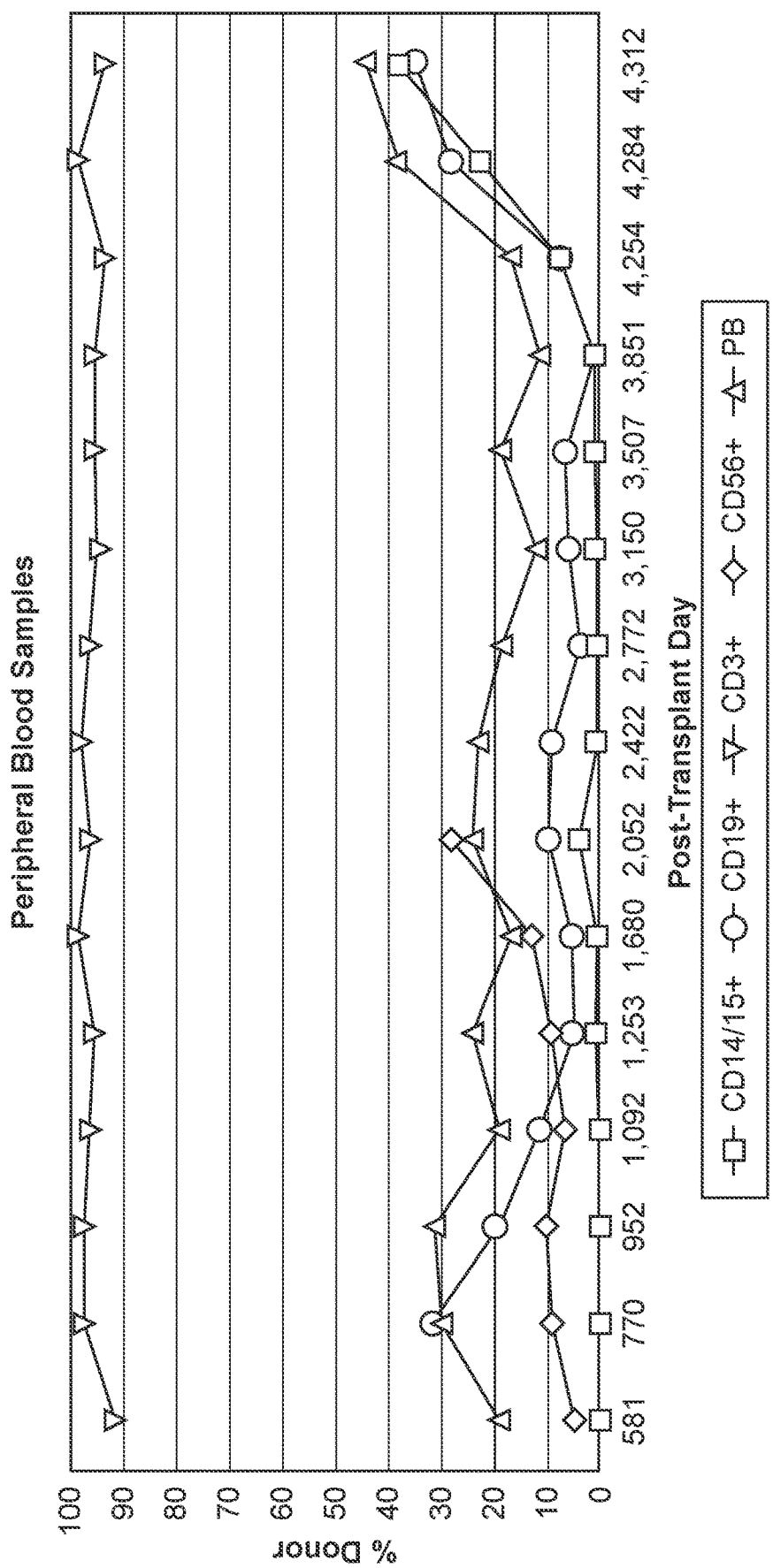
FIG. 10. Pt 4's Standard Of Care chimerism showing increasing donor chimerism after AMG 191 Conditioned HCT FIG. 11 AMG 191 depletes low risk MDS HSCs in vivo, as shown by human myeloid (human CD45$^+$CD13/33$^+$)

Remarkably, in the first dose cohort, beginning at 8-wks post-HCT, both Pts #1 and #2 had evidence of blood myeloid chimerism, the true measure of stem cell engraftment, which rose from 0% pre-procedure to >5% and has remained sustained a 1 year post-HCT (Table 3). Furthermore, both showed evidence of increasing CD19$^+$CD20$^+$ B cells (FIG. 9A). Pt #1 who pre-HCT had poor T cell levels and function has developed increased CD4 and CD8 T cells which are mainly naïve (FIG. 9B). Thus, she is making new T cells. Importantly, Pt 1 is markedly clinically improved, gaining weight and without diarrhea. She was well enough to start school. Pt #3 was very clinically fragile. In the post-transplant period he developed severe *C. difficile* colitis and then sepsis which were thought to be unrelated to the procedure. Chimerism studies show that Pt #3 did not engraft with myeloid cells. However, he has evidence of natural killer cell production which prior to procedure was not present. He has clinically improved, has gained weight and has increasing T cells. We conclude Pt #3 may have engrafted with a common lymphoid progenitor. The second dose level of 0.3 mg/kg has had a profound effect on HSC engraftment of Pt 4 whose most recent CD15+ cell chimerism level was 45%. Pt #4 B cell chimerism which is tracking positively with the myeloid chimerism, indicating that she will make adequate numbers of functional B cells.

These data show that even at a single very low dose of 0.1-0.3 mg/kg, AMG 191 clears sufficient HSC niche space to permit HSC engraftment with multilineage reconstitution in patients with SCID. Given the current trajectory we of our trial, we anticipate that higher doses will result in better engraftment leading us to conclude that this non-toxic stem cell therapy will prove curative of SCID.

Example 4

Anti-Human CD117 Antibodies Mediate Clearance of Myelodysplastic Syndrome Hematopoietic Stem Cells and Facilitate Establishment of Normal Hematopoiesis in Transplantation MDS arises from abnormal hematopoietic stem cells. The only potentially curative therapy available for MDS patients in hematopoietic stem cell transplantation (HCT) but relapse is common, likely due to the inability of current therapies to effectively eliminate disease-causing MDS HSCs. We show that MDS HSCs express cell-surface molecule CD117 (c-kit), a cytokine receptor that is also expressed on normal human HSCs. Anti-mouse CD117 monoclonal antibodies have been previously shown to deplete normal human HSCs and hematopoietic progenitor cells, creating niche space that permit donor HSC engraftment. We have now identified anti-human CD117 antibodies SR-1 and AMG191, which can not only deplete normal human HSCs, but also deplete MDS HSCs in an in vivo xenograft mouse model of MDS. In immunodeficient NOD/SCID/IL-2Ry null (NSG) mice stably engrafted with purified MDS HSCs from primary human MDS samples, treatment with anti-human CD117 antibodies reduced human MDS chimerism by 90% (P<0.01), whereas treatment with isotype control antibody had no significant effect on human MDS chimeras. In NSG mice engrafted with MDS HSCs from Revise International Protocol Scoring System (IPSS-R) very low risk and low risk MDS patients (n=4), human MDS chimerism was initially reduced by >90%, P, 0.01), as assessed one day after completion of treatment with anti-human CD117 antibodies, but human MDS chimerism rebounded to within +/−10% of baseline by 8 weeks after completion of treatment with anti-human CD117 antibodies, suggesting that MDS HSCs were able to recover despite the treatment. However, when we transplanted a second normal human HSC graft into these mice one week after completion of treatment with the antibodies, MDS cells were unable to recover and there was evidence of normal human hematopoiesis in the xenografts. These data suggest that transplantation of normal human HSCs was able to suppress the recovery of MDS HSCs. In conclusion, we show that anti-human CD117 antibodies have the potential to replace or augment the myeloablative component of HCT conditioning for MDS by depleting MDS HSCs and enhancing donor HSC engraftment.

Figure 11:
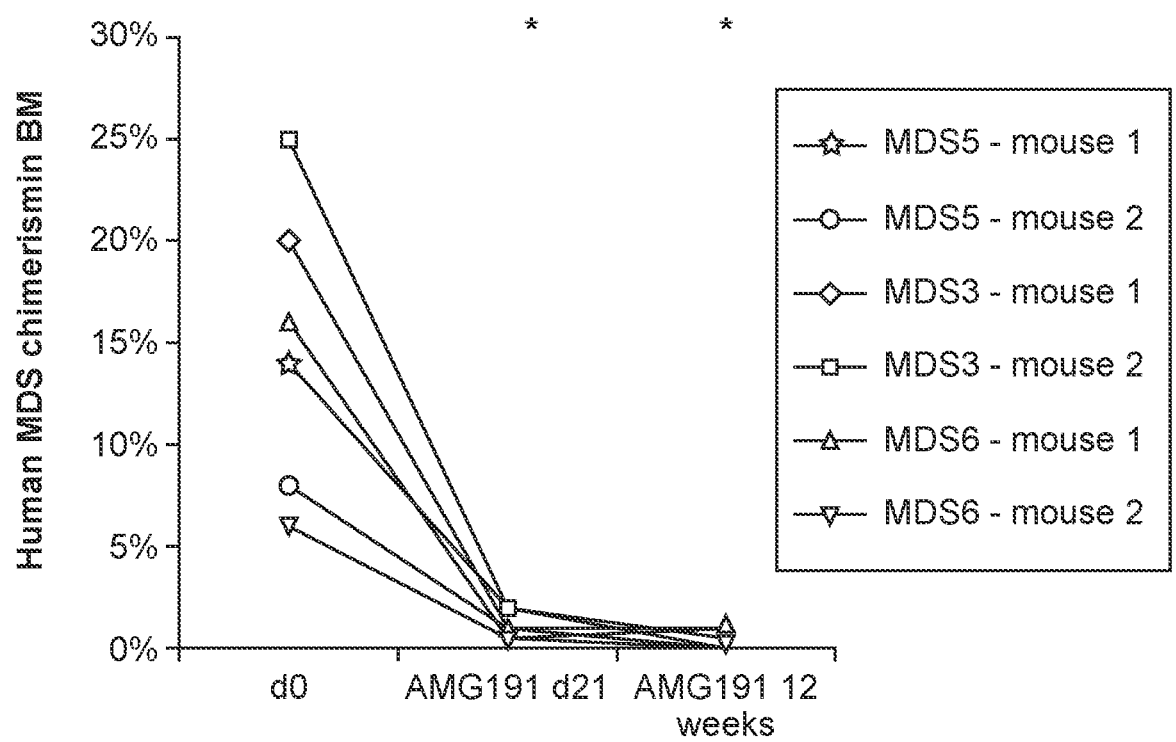

Specifically, we have evaluated the ability of AMG191 to deplete MDS HSCs in vivo in mice bearing MDS xenografts. A large single dose of 75 µg of AMG 191 (equivalent to 3 mg/kg) can significantly deplete MDS cells in vivo and thus reduce MDS cell burden in the xenografted mice, shown in FIG. 11.

Example 5

Replacement of endogenous hematopoietic stem cells (HSC) by transplantation of allogeneic donor or autologous gene-modified cells is curative therapy for a vast number of inherited and acquired disorders. The HCT procedure has two major components: (1) collection and preparation of hematopoietic grafts that contain the stem cells capable of replacing long-term blood formation in the patient (recipient); and (2) preparation of the recipient with treatments that will allow the transplanted hematopoietic cells to permanently engraft.

Allogeneic HCTs can be highly successful. However, the risks are substantial with conventional preparation. For the hematologic diseases of myelodysplastic syndromes (MDS) and acute myelogenous leukemia (AML) arising from MDS the only curative therapy is allogeneic HCT. However because MDS/AML are diseases of older adults, these individuals are particularly vulnerable to the toxicities of the transplant, and relatively few undergo this treatment. Furthermore, the inability to tolerate the procedure itself tolerability and unfavorable disease biology results in inferior survival following HCT for older adults with MDS and AML relative to younger adults.

Non-myeloablative (NMA) conditioning therapy prior to transplantation represents a strategy that has significantly improved HCT tolerability in older adults. NMA for MDS and AML involves administration of reduced doses of radiation and/or chemotherapy to confer some eradication of malignant clones and allow donor allogeneic HSC to engraft. The NMA approach capitalizes on graft-versus-tumor effects of donor hematopoietic and immune cell replacement. However, because of the relatively weaker effect of NMA HCT compared to conventional intensive HCT conditioning, relapses rates are higher in NMA recipients.

Presented here is a protocol to improve the efficacy of NMA allogeneic HCT with minimal toxicity for patients with MDS and AML by administering an antibody that targets endogenous normal and disease initiating HSC to augment engraftment in combination with a non-myeloablative conditioning regimen.

MDS are clonal myeloid disorders affecting the bone marrow and blood formation. MDS are primarily diseases of older adults, with 80% of cases diagnosed in adults over the age of 70 years. MDS are classified by the World Health Organization (WHO) guidelines. Prognostication is performed based upon scoring systems such as the International Prognostic Scoring System (IPSS) or the Revised IPSS (IPSS-R) which take into account risk factors such as cytogenetics, cytopenias, and percentage of marrow blasts. Using these prognostic scoring systems, patients can be segregated into low, intermediate, and high risk MDS, with corresponding likelihoods of survival in the absence of therapy. For example, whereas the median survival of untreated patient with low risk MDS is 5 to 6 years following diagnosis, those with high risk MDS have a high likelihood of rapidly evolving into AML and have an associated survival expectancy of less than six months from the time of diagnosis.

AML is a hematologic malignancy characterized by rapid expansion of clonal myeloid progenitor cells in the bone marrow. AML is the most commonly diagnosed acute leukemia in adults, and accounts for approximately 10,000 deaths per year in the United States. The median age at diagnosis is 67 years, characterizing AML as a disease of predominantly older adults. AML risk stratification is based largely on the cytogenetic and molecular genetic features at diagnosis. Age at diagnosis has emerged as an important prognostic feature, as older adults uniformly have inferior outcomes relative to younger adults regardless of leukemia cell characteristics. Additionally, older adults with AML are more likely to harbor unfavorable cytogenetic and molecular features, to have AML with dysplastic features, and to have therapy-related AML, all of which portend poor prognosis.

Allogeneic HCT is the only curative therapy for MDS and many forms of AML. Based upon the long latency and favorable survival associated with low risk MDS, HCT is typically offered to advanced, or higher risk MDS patients, where HCT has been shown to confer significant improvements in overall survival (OS). The standard approach to AML treatment includes induction followed by consolidation therapy. Given the poor survival rates for high risk and relapsed AML with chemotherapy consolidation, allogeneic HCT is recommended in first remission (CR1) for many patients with intermediate and poor-risk AML. The outcomes of allogeneic HCT for patients with AML and MDS depend upon several features, including disease risk, host features such as age and comorbidities, and transplant characteristics such as the donor and intensity of conditioning regimen administered.

The dismal outcomes of AML in older adults following standard chemotherapy has led to recommendations to consider allogeneic HCT for older adults who are appropriate candidates. The majority of older adults with AML will not be candidates for intensive myeloablative conditioning therapy prior to HCT and will therefore receive NMA conditioning regimens. The benefit of NMA HCT is derived from donor immune mediated graft versus tumor reactions. NMA regimens have been developed that shifted the burden of disease control from high doses of chemo-radiotherapy to the donor immune system. These NMA conditioning regimens have allowed older patients and those with medical co-morbidities to proceed with HCT. However, although NMA allogeneic HCT is associated with greater tolerability and fewer side effects in older adults with AML, higher rates of post-HCT relapse are observed with NMA as opposed to myeloablative HCT.

In order to allow older and less fit patients to receive allogeneic HCT, a chemotherapy-free low-intensity HCT conditioning regimen composed of total lymphoid irradiation in combination with anti-thymocyte globulin (TLI/ATG) is used. This regimen is well tolerated, with acute and chronic GVHD rates of <10% at one year, and similar non-relapse mortality (NRM) of <10% in both younger and older adults. A consequence of low intensity conditioning with TLI/ATG is that host hematopoietic and immune cells persist and result in a state of mixed hematopoietic and lymphoid chimerism (MC) that may convert to full donor chimerism (FDC) over a variable time course. The relapse risk is significantly higher in patients with persistent MC compared to those with FDC. Greater clearance of bone marrow HSCs following TLI/ATG conditioning may enhance engraftment and early donor chimerism, leading to reductions in AML and MDS relapse with this approach.

Although TLI/ATG as NMA HCT conditioning can prepare recipients for allogeneic HCT, TLI/ATG spares large areas of the bone marrow. Therefore, normal as well as MDS/AML HSCs in shielded bone marrow spaces are not directly exposed to radiation during TLI and therefore not directly targeted for elimination. We tested whether anti-mouse CD117 antibody (ACK2) was able to facilitate depletion of normal HSCs when given in conjunction with TLI/ATG. We found that ACK2, when administered before the commencement of TL/ATG and again after the completion of ATG, was able to deplete HSCs in shielded femoral bone marrow of TLI/ATG-treated mice, shown in FIG. 11.

The dosing schema and escalation is based upon preclinical work demonstrating that maximum stem cell clearance is achieved at higher doses of AMG 191. The timing of administration and pharmacokinetic (PK) collection is based on nonclinical data from non-human primates (NHPs) and simulations from Phase 1 clinical study estimating the predicted half-life ($t_{1/2}$) over the four dose levels. Available PK results reported for each patient in real-time is used to iteratively model the patient's estimated terminal tx in order to predict the time to AMG 191 clearance of <100 ng/mL.

Safety and dose escalation study to evaluate AMG 191 in combination with TLI/ATG as HCT conditioning therapy in adult subjects with MDS or secondary AML. Subjects receive an IV infusion of AMG 191 15 days prior to scheduled donor cell infusion. TLI/ATG conditioning begins on Day −11 and concludes on Day −1. Serum concentrations of AMG 191 are collected and used to estimate drug half-life and clearance of AMG 191. Peripheral blood stem cells (PBSC) mobilized using granulocyte-colony stimulating factor (G-CSF) are collected via donor apheresis following standard procedures and infused into the subject on scheduled Day 0. The target exposure of AMG 191 on the day of stem cell infusion is defined at 100 ng/mL. Subjects are evaluated for toxicity and HCT outcomes.

Dose Escalation Algorithm. Four planned dose levels (0.3 mg/kg, 0.6 mg/kg, 0.9 mg/kg, 1.2 mg/kg) of AMG 191 are administered in escalating cohorts using a 3+3 sequential design. Starting with the lowest AMG 191 dose, the dose is escalated based on the absence of dose limiting toxicities (DLT). Patients are sequentially enrolled only when the previous patient has reached the target donor stem cell infusion date. Four weeks (28 days) must elapse after completion of donor cell infusion in the final subject in each dose cohort to allow for safety assessment before treating subjects on the next higher dose cohort level. While not a DLT the delay of donor stem cell infusion due to a lack of AMG 191 clearance is a key dosing outcome and will be referred to as a dose limiting event (DLE) to distinguish it from a toxicity (DLT) outcome. For the purposes of this study a DLE will be defined as a delay in actual or predicted clearance of AMG 191 below the threshold of 500 ng/mL resulting in delay of donor stem cell infusion of >3 days beyond the scheduled transplant Day 0.

For donors of allogeneic HSC, G-CSF is administered subcutaneously at a dose of approximately 16 μg/kg/day subcutaneously for 5 consecutive days. Apheresis occurs on the $5^{th}$ day following the start of G-CSF (bone marrow transplant [BMT] Day −1). Target CD34$^+$ count is >5×10$^6$/kg with minimum acceptable dose CD34$^+$ of >2×10°/kg. If after the first day of apheresis collection ($5^{th}$ day of G-CSF), the CD34$^+$ is <5×10$^6$/kg recipient weight, then the donor will undergo a second day collection (on BMT Day 0).

TLI is administered ten times in 120 cGy fractions on Day 11 through Day 7 and Day 4 through Day 1. TLI is administered from a 6 MeV linear accelerator (photon beam). The radiation field (four fields-two anterior and two posterior) includes all major lymphoid organs including the thymus, spleen, and lymph nodes. A radiation oncologist evaluates patients prior to conditioning to determine blocks and radiation ports. ATG (Thymoglobulin) is administered five times intravenously at 1.5 mg/kg/day from Day 11 through Day 7 for a total dose of 7.5 mg/kg. Thymoglobulin doses are based on the adjusted ideal body weight if the patient is greater than or equal to 15 kg over ideal body weight.

The donor hematopoietic cell infusion is planned on Transplant Day 0. Donor cell infusion requires that the serum level of AMG 191 fall below or be predicted to fall below 500 ng/mL. Serum AMG 191 levels are monitored using a validated ELISA assay and non-compartmental linear mixed effect PK modeling of AMG 191 half-life and clearance to estimate when the AMG 191 serum concentrations will fall below 500 ng/mL. Once AMG 191 drug levels are predicted to be at or below 500 ng/mL or are predicted to be at or below this level on the day of transplant, patients will receive their cell infusion. Blood samples to determine AMG 191 levels are drawn immediately prior to HSC infusion.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

What is claimed is:

1. A method of hematopoietic stem cell engraftment in a human patient, the method comprising:
    infusing said human with a human or humanized monoclonal antibody specific for CD117 at a dose of up to about 3 mg/kg;
    allowing serum levels of the antibody specific for CD117 to drop to a level of less than about 500 ng/ml;
    administering to the patient a cell composition enriched for CD34+ hematopoietic stem cells in a dose of at least about 3×105 CD34+ cells/kg;
    wherein sustained levels of blood myeloid chimerism of at least about 1% donor type CD15+ cells is obtained.

2. The method of claim 1, wherein the antibody specific for CD117 is AMG 191.

3. The method of claim 1, wherein the dose of antibody is up to 0.3 mg/kg; and is delivered in a single dose.

4. The method of claim 1, wherein the cell composition enriched for CD34+ hematopoietic stem cells is tandemly selected for CD34+CD9Q+ cells.

5. The method of claim 1, wherein the cell composition enriched for CD34+ hematopoietic stem cells is single enriched for expression of CD34+ cells, and wherein the dose is at least about 5×106 CD34+ cells/kg and containing not more than about 3×104 CD3+ cells/kg.

6. The method of claim 1 wherein the cell composition enriched for CD34+ hematopoietic stem cells is HLA matched to the recipient.

7. The method of claim 1 wherein the cell composition enriched for CD34+ hematopoietic stem cells is haplotype identical to the recipient.

8. The method of claim 1, wherein the serum levels of the antibody specific for CD117 are less than about 10 ng/ml before administering the cell composition enriched for CD34+ hematopoietic stem cells.

9. The method of claim 1, wherein the serum levels of the antibody specific for CD117 are less than about 5 ng/ml before administering the cell composition enriched for CD34+ hematopoietic stem cells.

10. The method of claim 1, wherein the patient severe combined immunodeficiency (SCID).

11. The method of claim 1 wherein the patient has myelodysplastic syndrome (MDS).

12. The method of claim 1 wherein the patient has acute myelogenous leukemia (AML).

13. The method of claim 12, wherein the AML is secondary to MDS.

14. The method of claim 1, wherein the engraftment is performed in the absence of myeloablative conditioning.

15. The method of claim 1, wherein the engraftment is performed in the presence of non-myeloablative conditioning.

16. The method of claim 15, wherein the non-myeloablative conditioning comprises administration of an effective regimen of total lymphoid irradiation and anti-thymocyte globulin prior to engraftment.

17. The method of claim 16, wherein sustained levels of full hematopoietic chimerism is obtained.

* * * * *